(12) United States Patent
Short

(10) Patent No.: US 6,335,179 B1
(45) **Date of Patent: *Jan. 1, 2002**

(54) DIRECTED EVOLUTION OF THERMOPHILIC ENZYMES

(75) Inventor: Jay M. Short, Encinitas, CA (US)

(73) Assignee: Diversa Corporation, San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/185,373

(22) Filed: Nov. 3, 1998

Related U.S. Application Data

(63) Continuation of application No. 08/760,489, filed on Dec. 5, 1996, now Pat. No. 5,830,696.

(60) Provisional application No. 60/008,311, filed on Dec. 7, 1995.

(51) Int. Cl.[7] .......................... C12P 21/06; C07K 1/00

(52) U.S. Cl. ...................................... 435/69.1; 530/350

(58) Field of Search .......................... 435/69.1; 530/350

(56) References Cited

U.S. PATENT DOCUMENTS 5,830,696 A * 11/1998 Short ........................ 435/69.1

* cited by examiner

*Primary Examiner*—Hankyel T. Park

(74) *Attorney, Agent, or Firm*—Gray Cary Ware & Freidenrich LLP; Lisa A. Haile

(57) ABSTRACT

Thermostable enzymes are subjected to mutagenesis to produce a thermophilic enzyme which is stable at thermophilic temperature and which has increased activities at least two-fold higher than the activity of the wild-type thermostable enzyme at lower temperatures, which are temperatures of 50° C. or lower.

15 Claims, 3 Drawing Sheets

```
   1 ATG CTA CCA GAA GGC TTT CTC TGG GGC GTG TCC CAG TCC GGC TTT CAG TTC GAG ATG GGC   60
   1 Met Leu Pro Glu Gly Phe Leu Trp Gly Val Ser Gln Ser Gly Phe Gln Phe Glu Met Gly   20

  61 GAC AAG CTC AGG AGG AAC ATT GAT CCG AAC ACA GAC TGG TGG AAG TGG GTC AGG GAT CCC  120
  21 Asp Lys Leu Arg Arg Asn Ile Asp Pro Asn Thr Asp Trp Trp Lys Trp Val Arg Asp Pro   40

 121 TTC AAC ATA AAG AGG GAA CTC GTC AGC GGC GAC CTG CCC GAG GAG GGG ATA AAC AAC TAC  180
  41 Phe Asn Ile Lys Arg Glu Leu Val Ser Gly Asp Leu Pro Glu Glu Gly Ile Asn Asn Tyr   60

 181 GAA CTT TAC GAG AAG GAT CAC CCC CTC GCC AGA GAC CTC GGT CTG AAC GTT TAC AGG ATT  240
  61 Glu Leu Tyr Glu Lys Asp His Pro Leu Ala Arg Asp Leu Gly Leu Asn Val Tyr Arg Ile   80

 241 GGA ATA GAG TGG AGC AGG ATC TTT CCC TGG CCA ACC TGG TTT GTG GAG GTT GAC GTT GAA  300
  81 Gly Ile Glu Trp Ser Arg Ile Phe Pro Trp Pro Thr Trp Phe Val Glu Val Asp Val Glu  100

 301 CGG GAC AGC TAC GGA CTC GTG AAG GAC GTC AAA ATC GAT AAA GAC ACG CTC GAA GAG CTC  360
 101 Arg Asp Ser Tyr Gly Leu Val Lys Asp Val Lys Ile Asp Lys Asp Thr Leu Glu Glu Leu  120

 361 GAC GAG ATA GCG AAT CAT CAG GAG ATA GCC TAC TAC CGC CGC GTT ATA GAG CAC CTC AGG  420
 121 Asp Glu Ile Ala Asn His Gln Glu Ile Ala Tyr Tyr Arg Arg Val Ile Glu His Leu Arg  140

 421 GAG CTG GGC TTC AAG GTC ATC GTG AAC CTC AAC CAC TTC ACG CTC CCC CTC TGG CTT CAC  480
 141 Glu Leu Gly Phe Lys Val Ile Val Asn Leu Asn His Phe Ghr Leu Pro Leu Trp Leu His  160

 481 GAT CCG ATA ATC GCG AGG GAG AAG GCC CTC ACC AAC GGT AGG ATT GGC TGG GTC GGG CAG  540
 161 Asp Pro Ile Ile Ala Arg Glu Lys Ala Leu Thr Asn Gly Arg Ile Gly Trp Val Gly Gln  180

 541 GAG AGC GTG GTG GAG TTC GCC AAC TAC GCG GCG TAC ATC GCG AAC GCA CTC GGG GAC CTC  600
 181 Glu Ser Val Val Glu Phe Ala Lys Tyr Ala Ala Tyr Ile Ala Asn Ala Leu Gly Asp Leu  200

 601 GTT GAT ATG TGG AGC ACC TTC AAC GAR CCG ATG GTC GTT GTG GAN CTC GGT TAC CTC GCG  660
 201 Val Asp Met Trp Ser Thr Phe Asn Glu Pro Met Val Val Val Xxx Leu Gly Tyr Leu Ala  220

 661 CCC TAC TCC GGY TTT CCN CCG GGG GTT ATG AAC CCC GAG GCG GMN AAN CTG GCA ATC CTC  720
 221 Pro Tyr Ser Gly Phe Pro Pro Gly Val Met Asn Pro Glu Ala Xxx Xxx Leu Ala Ile Leu  240

 721 AAC ATG ATA AAC GCC CAC GCA CTG GCC TAC AAG ATG ATA AAG AAG TTC GAC AGG GTA AAG  780
 241 Asn Met Ile Asn Ala His Ala Leu Ala Tyr Lys Met Ile Lys Lys Phe Asp Arg Val Lys  260

 781 GCC GAT AAG GAT TCC CGC TCC GAG GCC GAG GTC GGG ATA ATC TAC AAC AAC ATA GGC GTT  840
 261 Ala Asp Lys Asp Ser Arg Ser Glu Ala Glu Val Gly Ile Ile Tyr Asn Asn Ile Gly Val  280

 841 NCC TAT CCA NAC GAC TCC AAC GAC CCN AAG GAC CTG AAA NCT NCA GAA AAC GAC AAC TAC  900
 281 Xxx Tyr Pro Xxx Asp Ser Asn Asp Pro Lys Asp Val Lys Xxx Xxx Glu Asn Asp Asn Tyr  300

 901 TTC CAC AGC GGG CTC TTC TTC GAC GCA ATC CAC AAG GGC AAG CTC AAC ATC GAG TTC GAC  960
 301 Phe His Ser Gly Leu Phe Phe Asp Ala Ile His Lys Gly Lys Leu Asn Ile Glu Phe Asp  320

 961 GGT GAG ACC TTC GTC AAA GTT CGG CAT CTC AGG GGG AAC GAC TGG ATA GGC GTT AAC TAC 1020
 321 Gly Glu Thr Phe Val Lys Val Arg His Leu Arg Gly Asn Asp Trp Ile Gly Val Asn Tyr  340

1021 TAC ACG AGA GAA GTC GTC AGG TAT TCG GAG CCC AAG TTC CCG AGC ATA CCC CTG ATA TCC 1080
 341 Tyr Thr Arg Glu Val Val Arg Tyr Ser Glu Pro Lys Phe Pro Ser Ile Pro Leu Ile Ser  360

1081 TTC CGG GGA GTT CAC AAC TAC GGT TAC GCC TGC AGG CCC GGG AGT TCT TCC GCC GAC GGA 1140
 361 Phe Arg Gly Val His Asn Tyr Gly Tyr Ala Cys Arg Pro Gly Ser Ser Ser Ala Asp Gly  380

1141 AGG CCC GTA AGC GAC ATC GGC TGG GAG ATC TAT CCG GAG GGG ATC TAC GAC TCG ATA AGA 1200
 381 Arg Pro Val Ser Asp Ile Gly Trp Glu Ile Tyr Pro Glu Gly Ile Tyr Asp Ser Ile Arg  400

1201 GAG GCC AAC AAA TAC GGG GTC CCG GTT TAC GTC ACC GAA AAC GGA ATA GCC GAT TCA ACT 1260
 401 Glu Ala Asn Lys Tyr Gly Val Pro Val Tyr Val Thr Glu Asn Gly Ile Ala Asp Ser Thr  420

1261 GAC ACC CTG CGG CCG TAC TAC CTC GCG AGC CAT GTA GCG AAG ATT GAG GAG GCG TAC GAG 1320
 421 Asp Thr Leu Arg Pro Tyr Tyr Leu Ala Ser His Val Ala Lys Ile Glu Glu Ala Tyr Glu  440

1321 GCG GGT TAC GAC GTC AGG GGC TAC CTC TAC TGG GCG CTG ACC GAC AAC TAC GAG TGG GCC 1380
 441 Ala Gly Tyr Asp Val Arg Gly Tyr Leu Tyr Trp Ala Leu Thr Asp Asn Tyr Glu Trp Ala  460

1381 CTC GGT TTC AGG ATG AGG TTC GGC CTC TAT AAA GTG GAT CTC ATA ACC AAG GAG AGA ACA 1440
 461 Leu Gly Phe Arg Met Arg Phe Gly Leu Tyr Lys Val Asp Leu Ile Thr Lys Glu Arg Thr  480

1441 CCG CGG GAG GAA AGC GTA AAG GTT TAT AGG GGC ATC GTG GAG AAC AAC GGA GTG AGC AAG 1500
 481 Pro Arg Glu Glu Ser Val Lys Val Tyr Arg Gly Ile Val Glu Asn Asn Gly Val Ser Lys  500

1501 GAA ATC CGG GAG AAG TTC GGA CTT GGG TGA   1530
 501 Glu Ile Arg Glu Lys Phe Gly Leu Gly End    510
```

```
  1 ATG CTA CCA GAA GGC TTT CTC TGG GGC GTG TCC CAG TCC GGC TTT CAG TTC GAG ATG GGC  60
  1 Met Leu Pro Glu Gly Phe Leu Trp Gly Val Ser Gln Ser Gly Phe Gln Phe Glu Met Gly  20

 61 GAC AAG CTC AGG AGG AAC ATT GAT CCG AAC ACA GAC TGG TGG AAG TGG GTC AGG GAT CCC 120
 21 Asp Lys Leu Arg Arg Asn Ile Asp Pro Asn Thr Asp Trp Trp Lys Trp Val Arg Asp Pro  40

121 TTC AAC ATA AAG AGG GAA CTC GTC AGC GGC GAC CTG CCC GAG GAG GGG ATA AAC AAC TAC 180
 41 Phe Asn Ile Lys Arg Glu Leu Val Ser Gly Asp Leu Pro Glu Glu Gly Ile Asn Asn Tyr  60

181 GAA CTT TAC GAG AAG GAT CAC CCC CTC GCC AGA GAC CTC GGT CTG AAC GTT TAC AGG ATT 240
 61 Glu Leu Tyr Glu Lys Asp His Pro Leu Ala Arg Asp Leu Gly Leu Asn Val Tyr Arg Ile  80

241 GGA ATA GAG TGG AGC AGG ATC TTT CCC TGG CCA ACC TGG TTT GTG GAG GTT GAC GTT GAA 300
 81 Gly Ile Glu Trp Ser Arg Ile Phe Pro Trp Pro Thr Trp Phe Val Glu Val Asp Val Glu 100

301 CGG GAC AGC TAC GGA CTC GTG AAG GAC GTC AAA ATC GAT AAA GAC ACG CTC GAA GAG CTC 360
101 Arg Asp Ser Tyr Gly Leu Val Lys Asp Val Lys Ile Asp Lys Asp Thr Leu Glu Glu Leu 120

361 GAC GAG ATA GCG AAT CAT CAG GAG ATA GCC TAC TAC CGC CGC GTT ATA GAG CAC CTC AGG 420
121 Asp Glu Ile Ala Asn His Gln Glu Ile Ala Tyr Tyr Arg Arg Val Ile Glu His Leu Arg 140

421 GAG CTG GGC TTC AAG GTC ATC GTG AAC CTC AAC CAC TTC ACG CTC CCC CTC TGG CTT CAC 480
141 Glu Leu Gly Phe Lys Val Ile Val Asn Leu Asn His Phe Ghr Leu Pro Leu Trp Leu His 160

481 GAT CCG ATA ATC GCG AGG GAG AAG GCC CTC ACC AAC GGT AGG ATT GGC TGG GTC GGG CAG 540
161 Asp Pro Ile Ile Ala Arg Glu Lys Ala Leu Thr Asn Gly Arg Ile Gly Trp Val Gly Gln 180
```

FIG. 1A

541 GAG AGC GTG GTG GAG TTC GCC AAG TAC GCG GCG TAC ATC GCG AAC GCA CTC GGG GAC CTC 600
181 Glu Ser Val Val Glu Phe Ala Lys Tyr Ala Ala Tyr Ile Ala Asn Ala Leu Gly Asp Leu 200

601 GTT GAT ATG TGG AGC ACC TTC AAC GAR CCG ATG GTC GTT GTG GAN CTC GGT TAC CTC GCG 660
201 Val Asp Met Trp Ser Thr Phe Asn Glu Pro Met Val Val Val Xxx Leu Gly Tyr Leu Ala 220

661 CCC TAC TCC GGY TTT CCN CCG GGG GTT ATG AAC CCC GAG GCG GMN AAN CTG GCA ATC CTC 720
221 Pro Tyr Ser Gly Phe Pro Pro Gly Val Met Asn Pro Glu Ala Xxx Xxx Leu Ala Ile Leu 240

721 AAC ATG ATA AAC GCC CAC GCA CTG GCC TAC AAG ATG ATA AAG AAG TTC GAC AGG GTA AAG 780
241 Asn Met Ile Asn Ala His Ala Leu Ala Tyr Lys Met Ile Lys Lys Phe Asp Arg Val Lys 260

781 GCC GAT AAG GAT TCC CGC TCC GAG GCC GAG GTC GGG ATA ATC TAC AAC AAC ATA GGC GTT 840
261 Ala Asp Lys Asp Ser Arg Ser Glu Ala Glu Val Gly Ile Ile Tyr Asn Asn Ile Gly Val 280

841 NCC TAT CCA NAC GAC TCC AAC GAC CCN AAG GAC CTG AAA NCT NCA GAA AAC GAC AAC TAC 900
281 Xxx Tyr Pro Xxx Asp Ser Asn Asp Pro Lys Asp Val Lys Xxx Xxx Glu Asn Asp Asn Tyr 300

901 TTC CAC AGC GGG CTC TTC TTC GAC GCA ATC CAC AAG GGC AAG CTC AAC ATC GAG TTC GAC 960
301 Phe His Ser Gly Leu Phe Phe Asp Ala Ile His Lys Gly Lys Leu Asn Ile Glu Phe Asp 320

961 GGT GAG ACC TTC GTC AAA GTT CGG CAT CTC AGG GGG AAC GAC TGG ATA GGC GTT AAC TAC 1020
321 Gly Glu Thr Phe Val Lys Val Arg His Leu Arg Gly Asn Asp Trp Ile Gly Val Asn Tyr 340

1021 TAC ACG AGA GAA GTC GTC AGG TAT TCG GAG CCC AAG TTC CCG AGC ATA CCC CTG ATA TCC 1080
341 Tyr Thr Arg Glu Val Val Arg Tyr Ser Glu Pro Lys Phe Pro Ser Ile Pro Leu Ile Ser 360

FIG. 1B

```
1081 TTC CGG GGA GTT CAC AAC TAC GGT TAC GCC TGC AGG CCC GGG AGT TCT TCC GCC GAC GGA 1140
 361 Phe Arg Gly Val His Asn Tyr Gly Tyr Ala Cys Arg Pro Gly Ser Ser Ser Ala Asp Gly  380

1141 AGG CCC GTA AGC GAC ATC GGC TGG GAG ATC TAT CCG GAG GGG ATC TAC GAC TCG ATA AGA 1200
 381 Arg Pro Val Ser Asp Ile Gly Trp Glu Ile Tyr Pro Glu Gly Ile Tyr Asp Ser Ile Arg  400

1201 GAG GCC AAC AAA TAC GGG GTC CCG GTT TAC GTC ACC GAA AAC GGA ATA GCC GAT TCA ACT 1260
 401 Glu Ala Asn Lys Tyr Gly Val Pro Val Tyr Val Thr Glu Asn Gly Ile Ala Asp Ser Thr  420

1261 GAC ACC CTG CGG CCG TAC TAC CTC GCG AGC CAT GTA GCG AAG ATT GAG GAG GCG TAC GAG 1320
 421 Asp Thr Leu Arg Pro Tyr Tyr Leu Ala Ser His Val Ala Lys Ile Glu Glu Ala Tyr Glu  440

1321 GCG GGT TAC GAC GTC AGG GGC TAC CTC TAC TGG GCG CTG ACC GAC AAC TAC GAG TGG GCC 1380
 441 Ala Gly Tyr Asp Val Arg Gly Tyr Leu Tyr Trp Ala Leu Thr Asp Asn Tyr Glu Trp Ala  460

1381 CTC GGT TTC AGG ATG AGG TTC GGC CTC TAT AAA GTG GAT CTC ATA ACC AAG GAG AGA ACA 1440
 461 Leu Gly Phe Arg Met Arg Phe Gly Leu Tyr Lys Val Asp Leu Ile Thr Lys Glu Arg Thr  480

1441 CCG CGG GAG GAA AGC GTA AAG GTT TAT AGG GGC ATC GTG GAG AAC AAC GGA GTG AGC AAG 1500
 481 Pro Arg Glu Glu Ser Val Lys Val Tyr Arg Gly Ile Val Glu Asn Asn Gly Val Ser Lys  500

1501 GAA ATC CGG GAG AAG TTC GGA CTT GGG TGA  1530
 501 Glu Ile Arg Glu Lys Phe Gly Leu Gly End   510
```

FIG. 1C

SEQUENCE LISTING

```
(1) GENERAL INFORMATION:

   (iii) NUMBER OF SEQUENCES: 4


(2) INFORMATION FOR SEQ ID NO: 1:

     (i) SEQUENCE CHARACTERISTICS:
          (A) LENGTH: 4463 base pairs
          (B) TYPE: nucleic acid
          (C) STRANDEDNESS: single
          (D) TOPOLOGY: linear

    (ii) MOLECULE TYPE: Genomic DNA

    (ix) FEATURE:
          (A) NAME/KEY: Coding Sequence
          (B) LOCATION: 1...4461

    (xi) SEQUENCE DESCRIPTION: SEQ ID NO: 1:

AAT TCC AGG ATG AAC CTC ATC TGG TCG GTC TTG AGC TTG TAC ATT CCG        48
Asn Ser Arg Met Asn Leu Ile Trp Ser Val Leu Ser Leu Tyr Ile Pro
  1               5                  10                  15

GAA CCG ATG GGG TTC TCG CTG TTG GCG TAC TTT ATC GGG TCT TTG ATG        96
Glu Pro Met Gly Phe Ser Leu Leu Ala Tyr Phe Ile Gly Ser Leu Met
             20                  25                  30
```

-continued

```
TCC TTC CAG ATG TGC TCA GGG ACG ATC GGG ATC TGG AGC CAG TCC CAC      144
Ser Phe Gln Met Cys Ser Gly Thr Ile Gly Ile Trp Ser Gln Ser His
         35                  40                  45

TCC GCG TGC GGA TCG CTG AAG ATG AAA TCA ACG GTT CTG TCG TCA ACG      192
Ser Ala Cys Gly Ser Leu Lys Met Lys Ser Thr Val Leu Ser Ser Thr
     50                  55                  60

ACC TTG ACC TCC TTG AGC CAG CCC CAA ACG CTC GAG AAG GAG GCA CCG      240
Thr Leu Thr Ser Leu Ser Gln Pro Gln Thr Leu Glu Lys Glu Ala Pro
 65                  70                  75                  80

GTG TGG TTC TTC GCG AGG AAG GTG AAC TTA ACG TCT TCA GCG GTT AGG      288
Val Trp Phe Phe Ala Arg Lys Val Asn Leu Thr Ser Ser Ala Val Arg
                 85                  90                  95

GGC TTT CCG TCC TGC CAG GTT AGG CCC TCC TTC AGC TTG ACC TCG GTG      336
Gly Phe Pro Ser Cys Gln Val Arg Pro Ser Phe Ser Leu Thr Ser Val
            100                 105                 110

TTG TCG TTG ATC CAC TTC CCA GAC TCG GCC AGC CAG GGA ATG AGC TGG      384
Leu Ser Leu Ile His Phe Pro Asp Ser Ala Ser Gln Gly Met Ser Trp
        115                 120                 125

TCC TTC AGC GGG TCG AAG AAC AGG GGC TCG ATG AGG CTA TCG TGC CTG      432
Ser Phe Ser Gly Ser Lys Asn Arg Gly Ser Met Arg Leu Ser Cys Leu
    130                 135                 140

CTG CGG CCC AGG AGA CAA GGG GAT AGT TCG TCG GCT GAC TCC ACA GAC      480
Leu Arg Pro Arg Arg Gln Gly Asp Ser Ser Ser Ala Asp Ser Thr Asp
145                 150                 155                 160

CGC CTC CAA CGT AGA GGG TTT CAT TCC TGG GAA GCT CCT CGG CGC GGA      528
Arg Leu Gln Arg Arg Gly Phe His Ser Trp Glu Ala Pro Arg Arg Gly
                165                 170                 175

CGT AGC CCG CGA ATC CAA CAA GGC TTG AAA CCA TCA GCA CTG CCA GCA      576
Arg Ser Pro Arg Ile Gln Gln Gly Leu Lys Pro Ser Ala Leu Pro Ala
            180                 185                 190

GCA AAC CAA GGA TTC GTC TCA TGC GCA CCA CCC CAG ACC GCG AGG GTC      624
Ala Asn Gln Gly Phe Val Ser Cys Ala Pro Pro Gln Thr Ala Arg Val
        195                 200                 205

TGT AGT TAT AAA AAC GCG CTC CAA ATT TAT AAA ACT TTG GGT TCT GTT      672
Cys Ser Tyr Lys Asn Ala Leu Gln Ile Tyr Lys Thr Leu Gly Ser Val
    210                 215                 220

ATA AAA TTG GGG CAA AAA TTA AAA TCG GCA AAC CTT ATA AGG GAG AAA      720
Ile Lys Leu Gly Gln Lys Leu Lys Ser Ala Asn Leu Ile Arg Glu Lys
225                 230                 235                 240

GGC AAA GTT ACA TGG GGG TTG GTC TAT GCT ACC AGA AGG CTT TCT CTG      768
Gly Lys Val Thr Trp Gly Leu Val Tyr Ala Thr Arg Arg Leu Ser Leu
                245                 250                 255

GGG CGT GTC CCA GTC CGG CTT TCA GTT CGA GAT GGG CGA CAA GCT CAG      816
Gly Arg Val Pro Val Arg Leu Ser Val Arg Asp Gly Arg Gln Ala Gln
            260                 265                 270

GAG GAA CAT TCC GAA CAC AGA CTG GTG GAA GTG GGT CAG GGA TCC CTT      864
Glu Glu His Ser Glu His Arg Leu Val Glu Val Gly Gln Gly Ser Leu
        275                 280                 285

CAA CAT AAA GAG GGA ACT CGT CAG CGG CGA CCT GCC CGA GGA GGG GAT      912
Gln His Lys Glu Gly Thr Arg Gln Arg Arg Pro Ala Arg Gly Gly Asp
    290                 295                 300

AAA CAA CTA CGA ACT TTA CGA GAA GGA TCA CCG CCT CGC CAG AGA CCT      960
Lys Gln Leu Arg Thr Leu Arg Glu Gly Ser Pro Pro Arg Gln Arg Pro
305                 310                 315                 320

CGG TCT GAA CGT TTA CAG GAT TGG AAT AGA GTG GAG CAG GAT CTT TCC     1008
Arg Ser Glu Arg Leu Gln Asp Trp Asn Arg Val Glu Gln Asp Leu Ser
                325                 330                 335

CTG GCC AAC GTG GTT TGT GGA GGT CGT GCG GGA CAG CTA CGG ACT CGT     1056
Leu Ala Asn Val Val Cys Gly Gly Arg Ala Gly Gln Leu Arg Thr Arg
```

-continued

```
            340                 345                 350

GAA GGA CGT CAA AAT CGA AGA CAC GCT CGA AGA GCT CGA CGA GAT AGC      1104
Glu Gly Arg Gln Asn Arg Arg His Ala Arg Arg Ala Arg Arg Asp Ser
        355                 360                 365

GAA TCA TCA GGA GAT AGC CTA CTA CCG CCG CGT TAT AGA GCA CCT CAG      1152
Glu Ser Ser Gly Asp Ser Leu Leu Pro Pro Arg Tyr Arg Ala Pro Gln
    370                 375                 380

GGA GCT GGG CTT CAA GGT CAT CGT GAA CCT CAA CCA CTT CAC GCT CCC      1200
Gly Ala Gly Leu Gln Gly His Arg Glu Pro Gln Pro Leu His Ala Pro
385                 390                 395                 400

CCT CTG GCT TCA CGA TCC GAT AAT CGC GAG GGA GAA GGC CCT CAC CAA      1248
Pro Leu Ala Ser Arg Ser Asp Asn Arg Glu Gly Glu Gly Pro His Gln
                405                 410                 415

CGG GAT TGG CTG GGT CGG GCA GGA GAG CGT GGT GGA GTT CGC CAA GTA      1296
Arg Asp Trp Leu Gly Arg Ala Gly Glu Arg Gly Gly Val Arg Gln Val
            420                 425                 430

CGC GGC GTA CAT CGC GAA CGC ACT CGG GGA CCT CGT TAT GTG GAG CAC      1344
Arg Gly Val His Arg Glu Arg Thr Arg Gly Pro Arg Tyr Val Glu His
        435                 440                 445

CTT CAA CGA GCC GAT GGT CGT TGT GGA GCT CGG TTA CCT CGC GCC CTA      1392
Leu Gln Arg Ala Asp Gly Arg Cys Gly Ala Arg Leu Pro Arg Ala Leu
    450                 455                 460

CTC CGG CTT TCC GCC GGG GGT TAT GAA CCC CGA GGC GGC AAA GCT GGC      1440
Leu Arg Leu Ser Ala Gly Gly Tyr Glu Pro Arg Gly Gly Lys Ala Gly
465                 470                 475                 480

AAT CCT CAA CAT GAT AAA CGC CCA CGC ACT GGC CTA CAA GAT GAT AAA      1488
Asn Pro Gln His Asp Lys Arg Pro Arg Thr Gly Leu Gln Asp Asp Lys
                485                 490                 495

GAA GTT CGA CAG GGT AAA GGC CGA GGA TTC CCG CTC CGA GGC CGA GGT      1536
Glu Val Arg Gln Gly Lys Gly Arg Gly Phe Pro Leu Arg Gly Arg Gly
            500                 505                 510

CGG GAT AAT CTA CAA CAA CAT AGG CGT TGC CTA TCC ATA CGA CTC CAA      1584
Arg Asp Asn Leu Gln Gln His Arg Arg Cys Leu Ser Ile Arg Leu Gln
        515                 520                 525

CGA CCC AAA GGA CGT GAA AGC TGC AGA AAA CGA CAA CTA CTT CCA CAG      1632
Arg Pro Lys Gly Arg Glu Ser Cys Arg Lys Arg Gln Leu Leu Pro Gln
    530                 535                 540

CGG GCT CTT CTT CGA CGC AAT CCA CAA GGG CAA GCT CAA CAT CGA GTT      1680
Arg Ala Leu Leu Arg Arg Asn Pro Gln Gly Gln Ala Gln His Arg Val
545                 550                 555                 560

CGA CGG GAC CTT CGT CAA AGT TCG GCA TCT CAG GGG GAA CGA CTG GAT      1728
Arg Arg Asp Leu Arg Gln Ser Ser Ala Ser Gln Gly Glu Arg Leu Asp
                565                 570                 575

AGG CGT CTA CTA CAC GAG AGA AGT CGT CAG GTA TTC GGA GCC CAA GTT      1776
Arg Arg Leu Leu His Glu Arg Ser Arg Gln Val Phe Gly Ala Gln Val
            580                 585                 590

CCC GAG CAT ACC CCT GAT ATC CTT CCG GGG AGT TCA CAA CTA CGG CTA      1824
Pro Glu His Thr Pro Asp Ile Leu Pro Gly Ser Ser Gln Leu Arg Leu
        595                 600                 605

CGC CTG CAG GCC CGG GAG TTC TTC CGC CGA CGG AAG GCC CGT AAG CGA      1872
Arg Leu Gln Ala Arg Glu Phe Phe Arg Arg Arg Lys Ala Arg Lys Arg
    610                 615                 620

CAT CGG CTG GGA GAT CTA TCC GGA GGG GAT CTA CGA CTC GAT AAG AGA      1920
His Arg Leu Gly Asp Leu Ser Gly Gly Asp Leu Arg Leu Asp Lys Arg
625                 630                 635                 640

GGC CAA CAA ATA CGG GGT CCC GGT TTA CGT CAC CGA AAA CGG AAT AGC      1968
Gly Gln Gln Ile Arg Gly Pro Gly Leu Arg His Arg Lys Arg Asn Ser
                645                 650                 655

CGA TTC AAC CAC CCT GCG GCC GTA CTA CCT CGC GAG CCA TGT AGC GAA      2016
```

-continued

```
Arg Phe Asn His Pro Ala Ala Val Leu Pro Arg Glu Pro Cys Ser Glu
            660                 665                 670

GAT GGA GGC GTA CGA GGC GGG TTA CGA CGT CAG GGG CTA CCT CTA CTG     2064
Asp Gly Gly Val Arg Gly Gly Leu Arg Arg Gln Gly Leu Pro Leu Leu
        675                 680                 685

GGC GCT GAC CGA CAA CTA CGA GTG GGC CCT CGG TTT CAG GAT GAG GTT     2112
Gly Ala Asp Arg Gln Leu Arg Val Gly Pro Arg Phe Gln Asp Glu Val
    690                 695                 700

CGG CCT CTA AGT GGA TCT CAT AAC CAA GGA GAG AAC ACC GCG GGA GGA     2160
Arg Pro Leu Ser Gly Ser His Asn Gln Gly Glu Asn Thr Ala Gly Gly
705                 710                 715                 720

AAG CGT AAA GGT TTA GGG CAT CGT GGA GAA CAA CGG AGT GAG CAA GGA     2208
Lys Arg Lys Gly Leu Gly His Arg Gly Glu Gln Arg Ser Glu Gln Gly
            725                 730                 735

AAT CCG GGA GAA GTT CGG ACT TGG GTG AAG GTA ATG AAG ACG ATA GCC     2256
Asn Pro Gly Glu Val Arg Thr Trp Val Lys Val Met Lys Thr Ile Ala
            740                 745                 750

GTC GAT GAG GAC ACT TGG GAG GCA AGA AGC AGG TCA GGC TTG AGG CAG     2304
Val Asp Glu Asp Thr Trp Glu Ala Arg Ser Arg Ser Gly Leu Arg Gln
        755                 760                 765

ATC GTA CGA CGA AGT CCT GAA AAA GCT CAT ACA GGC CTG GAC AGG GTT     2352
Ile Val Arg Arg Ser Pro Glu Lys Ala His Thr Gly Leu Asp Arg Val
    770                 775                 780

GAC TCG ACA AGG CCG AGA GCG GCA ACG ACG AGG AGG CCG AGC TCA TGC     2400
Asp Ser Thr Arg Pro Arg Ala Ala Thr Thr Arg Arg Pro Ser Ser Cys
785                 790                 795                 800

TCA ACC TCA AGA ACA AGA AGA CGG GAG GAC AGG GTA ATG AAG AGA CTC     2448
Ser Thr Ser Arg Thr Arg Arg Arg Glu Asp Arg Val Met Lys Arg Leu
            805                 810                 815

CCT GAG AGG GTC TCT TTC GAT CCC GAG GCG TTC GTT GAG ATA AAC CGA     2496
Pro Glu Arg Val Ser Phe Asp Pro Glu Ala Phe Val Glu Ile Asn Arg
            820                 825                 830

AAG AGA AAC AGG GAC TTT TTA GAG TTC CTC TTG GCG GAG TTC CAG GTG     2544
Lys Arg Asn Arg Asp Phe Leu Glu Phe Leu Leu Ala Glu Phe Gln Val
        835                 840                 845

NCG GTT TCC TTC TTC ACG GTT CAT CCA TAC CTC CTC GGC AAG ACC TAT     2592
Xaa Val Ser Phe Phe Thr Val His Pro Tyr Leu Leu Gly Lys Thr Tyr
    850                 855                 860

CTG GGC AGG GAC CTG GAA AGC GAA GTT CGG GCC CTC AAC GAA GCC TAC     2640
Leu Gly Arg Asp Leu Glu Ser Glu Val Arg Ala Leu Asn Glu Ala Tyr
865                 870                 875                 880

ACC ATC GTG TAT CCC ACG AAA GAA CTC CTC ATG AGG GCC ATA GAA ATC     2688
Thr Ile Val Tyr Pro Thr Lys Glu Leu Leu Met Arg Ala Ile Glu Ile
            885                 890                 895

GAG GCG AGG CTG ATA AAA AGG GGA ATT TTT CTC TCT TTC GAC GAC ATC     2736
Glu Ala Arg Leu Ile Lys Arg Gly Ile Phe Leu Ser Phe Asp Asp Ile
            900                 905                 910

GTC ATT GGA GTA ACT GCC ATT GAA AAC AAC GCC CTT CTC GTG AGC TCT     2784
Val Ile Gly Val Thr Ala Ile Glu Asn Asn Ala Leu Leu Val Ser Ser
        915                 920                 925

GCC CCC TCA CGC TAC AGG CCC CTT GAG AAG TAC GGG CTC AAC GTT ATC     2832
Ala Pro Ser Arg Tyr Arg Pro Leu Glu Lys Tyr Gly Leu Asn Val Met
    930                 935                 940

GGG CTC AAG CTC CTT CTT CGA CGA ACT CCG GAA GCT CGC CCG GAA GGA     2880
Gly Leu Lys Leu Leu Leu Arg Arg Thr Pro Glu Ala Arg Pro Glu Gly
945                 950                 955                 960

AGC CGC CAG ATG GGA GGT GCC CCC GGT GGG ATC TTC TCC AGA ACG AGA     2928
Ser Arg Gln Met Gly Gly Ala Pro Gly Gly Ile Phe Ser Arg Thr Arg
            965                 970                 975
```

-continued

```
ATG AAC GCT ATC CTC GGG AAG AGC CAG CGG AGG CTT CTC GCC CTA AAG     2976
Met Asn Ala Ile Leu Gly Lys Ser Gln Arg Arg Leu Leu Ala Leu Lys
            980                 985                 990

CCC CTC TCC TCG AAC TCC CCC CTA AGC TCC TCC GGT GAG GGA AAG GCG     3024
Pro Leu Ser Ser Asn Ser Pro Leu Ser Ser Ser Gly Glu Gly Lys Ala
        995                1000                1005

TCT ATC GAG CTG ACA AGG TGT TCG GCT TTC TCG TTG CCC GTC GTC AGC     3072
Ser Ile Glu Leu Thr Arg Cys Ser Ala Phe Ser Leu Pro Val Val Ser
   1010                1015                1020

TTT CCG ATG AGG GGA ACA ACC GTT CTC GTG AGC CAG GCC ATC TTT CCA     3120
Phe Pro Met Arg Gly Thr Thr Val Leu Val Ser Gln Ala Ile Phe Pro
025                1030                1035                1040

AGG AGC GAG GGG TTC TTT GAG AAC TCG AGG ATT ACG AGC CTT CCT CCC     3168
Arg Ser Glu Gly Phe Phe Glu Asn Ser Arg Ile Thr Ser Leu Pro Pro
               1045                1050                1055

GGC TTC AGA ACA CGG TGG AGC TCC TCT ATA GCT TTT TCC CTA TCG GAG     3216
Gly Phe Arg Thr Arg Trp Ser Ser Ser Ile Ala Phe Ser Leu Ser Glu
           1060                1065                1070

AAG NTT CTG AGG TCG GAG GCG ACG CTG ACA ATG TCG NAG CTC CCG TCC     3264
Lys Xaa Leu Arg Ser Glu Ala Thr Leu Thr Met Ser Xaa Leu Pro Ser
       1075                1080                1085

GGA GNC ATT TCT TCC GCC CTG CCA ACG CTC AGC CTC GCG NAG GGG ACC     3312
Gly Xaa Ile Ser Ser Ala Leu Pro Thr Leu Ser Leu Ala Xaa Gly Thr
   1090                1095                1100

TTT CTC CCC GCT ATC CTG AGC ATC TCC TCG CTG CAG TCG AGG CCG AAC     3360
Phe Leu Pro Ala Ile Leu Ser Ile Ser Ser Leu Gln Ser Arg Pro Asn
105                1110                1115                1120

TAC GCC CGA CAG GTT TCT CTT TTC AAG CCT CTT CCT CAT GCA GAG CAT     3408
Tyr Ala Arg Gln Val Ser Leu Phe Lys Pro Leu Pro His Ala Glu His
               1125                1130                1135

CAT GTC CCT GGT TCC GCA GGC CAC GTC AAG GAT TTT CGG CCT TTC GCG     3456
His Val Pro Gly Ser Ala Gly His Val Lys Asp Phe Arg Pro Phe Ala
           1140                1145                1150

AAC CTC AAG GGA CTT CAA AAC CTC CTC GCA GGC CTT TTT CCT CCA CAA     3504
Asn Leu Lys Gly Leu Gln Asn Leu Leu Ala Gly Leu Phe Pro Pro Gln
       1155                1160                1165

CCT GTC GAG ACT GAG GCT TAT CAG CCT GTT GGT ATC GTA GCG CTC CGC     3552
Pro Val Glu Thr Glu Ala Tyr Gln Pro Val Gly Ile Val Ala Leu Arg
   1170                1175                1180

AAT GCT GTC AAA GAG CTC CCT TAC CAA GCT CCT CCC TCC CGA GGA CCT     3600
Asn Ala Val Lys Glu Leu Pro Tyr Gln Ala Pro Pro Ser Arg Gly Pro
185                1190                1195                1200

TCT TTA TCT TCG CGG GCC TTC CGC CTA GGT AAA CCC TGT CCG CAA TTT     3648
Ser Leu Ser Ser Arg Ala Phe Arg Leu Gly Lys Pro Cys Pro Gln Phe
               1205                1210                1215

AGA GCT CCT CGA GCT GGT GCG AGA CGA CCA GAA CGC CTT TTC CAG AAT     3696
Arg Ala Pro Arg Ala Gly Ala Arg Arg Pro Glu Arg Leu Phe Gln Asn
           1220                1225                1230

TGG CTA ATT CCC GAA TTA TGG AAA GAA GTT CTT CTT TGG AGC GCG CGT     3744
Trp Leu Ile Pro Glu Leu Trp Lys Glu Val Leu Leu Trp Ser Ala Arg
       1235                1240                1245

CGA GGC CGG AGG GCT CGT CCA GAA TCA GGA CAT CGA AGT CCA GCA GGG     3792
Arg Gly Arg Arg Ala Arg Pro Glu Ser Gly His Arg Ser Pro Ala Gly
   1250                1255                1260

CGC GCA GGA GAG AAG TTT TTC TCC TCG TCC CCC CGC TCA CTT CCT TTG     3840
Arg Ala Gly Glu Lys Phe Phe Ser Ser Ser Pro Arg Ser Leu Pro Leu
265                1270                1275                1280

GAT AGA GGT CGA GGT AGT TCT CCA GGC CGA GTC TCT CCA CGT ATT CGA     3888
Asp Arg Gly Arg Gly Ser Ser Pro Gly Arg Val Ser Pro Arg Ile Arg
               1285                1290                1295
```

-continued

```
GCC TGC ACT CCC TTC CCC AGC GGG CCG GCA GGC AGA CGT TGT CCC GCC      3936
Ala Cys Thr Pro Phe Pro Ser Gly Pro Ala Gly Arg Arg Cys Pro Ala
           1300                1305                1310

TCT TCC ACG GCA GAA GGT AGT CCT CCT GAT AGA GGA CGG AGG GGT TCT      3984
Ser Ser Thr Ala Glu Gly Ser Pro Pro Asp Arg Gly Arg Arg Gly Ser
       1315                1320                1325

TCA CAA AGA CCT CGC CCG AGT CCG GGT TCT CAA CTC CGG CCA AAA TCT      4032
Ser Gln Arg Pro Arg Pro Ser Pro Gly Ser Gln Leu Arg Pro Lys Ser
   1330                1335                1340

TCA CGA GGG TGC TCT TTC CCG TCC CGT TCG GCC CGA GGC CGA CCA CCT      4080
Ser Arg Gly Cys Ser Phe Pro Ser Arg Ser Ala Arg Gly Arg Pro Pro
345                 1350                1355                1360

CGC CGG CCC CCT CAA GGC CCC CGT CGA GTA TGG GCT CAC AGG ACT TTC      4128
Arg Arg Pro Pro Gln Gly Pro Arg Arg Val Trp Ala His Arg Thr Phe
               1365                1370                1375

GGT TCT TCA CCA GTA CCA GCC TTT CAC CCA TTC CTC GAC CTC CTC AGA      4176
Gly Ser Ser Pro Val Pro Ala Phe His Pro Phe Leu Asp Leu Leu Arg
           1380                1385                1390

AGT AGC TGG TCG AGG GTT ATC ATG AGC AGG ATT AAG AGC AGT GCC CAG      4224
Ser Ser Trp Ser Arg Val Ile Met Ser Arg Ile Lys Ser Ser Ala Gln
       1395                1400                1405

GCA AAA ACA CCG GCT TTA ATT CCC AAA TCG GAG ACG AGC TGG CCG ATT      4272
Ala Lys Thr Pro Ala Leu Ile Pro Lys Ser Glu Thr Ser Trp Pro Ile
   1410                1415                1420

CCT CCC GCT GAA CCA AAA GCC TCG GCA ACG ACG CTT ATC CTG AGC GCT      4320
Pro Pro Ala Glu Pro Lys Ala Ser Ala Thr Thr Leu Ile Leu Ser Ala
425                 1430                1435                1440

ATT CCC AGG GCG ACT CTG CCT GCC GAG ACC ATC TCG GGG AGC GTT CCC      4368
Ile Pro Arg Ala Thr Leu Pro Ala Glu Thr Ile Ser Gly Ser Val Pro
               1445                1450                1455

GGG ACG ATG AAG TGC CGG AGC AGC TTT GAG GGT TTG AGG AGA ACT ATC      4416
Gly Thr Met Lys Cys Arg Ser Ser Phe Glu Gly Leu Arg Arg Thr Ile
           1460                1465                1470

AGC GGG CGG TAT TTT TCT ATC ACC TTT TCG CTT GAG CTC ACT CCA GC       4463
Ser Gly Arg Tyr Phe Ser Ile Thr Phe Ser Leu Glu Leu Thr Pro
       1475                1480                1485
```

(2) INFORMATION FOR SEQ ID NO: 2:

(i) SEQUENCE CHARACTERISTICS:
(A) LENGTH: 1487 amino acids
(B) TYPE: amino acid
(D) TOPOLOGY: linear (ii) MOLECULE TYPE: protein (v) FRAGMENT TYPE: internal (xi) SEQUENCE DESCRIPTION: SEQ ID NO: 2:

```
Asn Ser Arg Met Asn Leu Ile Trp Ser Val Leu Ser Leu Tyr Ile Pro
  1               5                  10                  15

Glu Pro Met Gly Phe Ser Leu Leu Ala Tyr Phe Ile Gly Ser Leu Met
             20                  25                  30

Ser Phe Gln Met Cys Ser Gly Thr Ile Gly Ile Trp Ser Gln Ser His
         35                  40                  45

Ser Ala Cys Gly Ser Leu Lys Met Lys Ser Thr Val Leu Ser Ser Thr
     50                  55                  60

Thr Leu Thr Ser Leu Ser Gln Pro Gln Thr Leu Glu Lys Glu Ala Pro
 65                  70                  75                  80

Val Trp Phe Phe Ala Arg Lys Val Asn Leu Thr Ser Ser Ala Val Arg
```

-continued

```
                85                  90                  95

Gly Phe Pro Ser Cys Gln Val Arg Pro Ser Phe Ser Leu Thr Ser Val
            100                 105                 110

Leu Ser Leu Ile His Phe Pro Asp Ser Ala Ser Gln Gly Met Ser Trp
        115                 120                 125

Ser Phe Ser Gly Ser Lys Asn Arg Gly Ser Met Arg Leu Ser Cys Leu
    130                 135                 140

Leu Arg Pro Arg Arg Gln Gly Asp Ser Ser Ser Ala Asp Ser Thr Asp
145                 150                 155                 160

Arg Leu Gln Arg Arg Gly Phe His Ser Trp Glu Ala Pro Arg Arg Gly
                165                 170                 175

Arg Ser Pro Arg Ile Gln Gln Gly Leu Lys Pro Ser Ala Leu Pro Ala
            180                 185                 190

Ala Asn Gln Gly Phe Val Ser Cys Ala Pro Pro Gln Thr Ala Arg Val
        195                 200                 205

Cys Ser Tyr Lys Asn Ala Leu Gln Ile Tyr Lys Thr Leu Gly Ser Val
    210                 215                 220

Ile Lys Leu Gly Gln Lys Leu Lys Ser Ala Asn Leu Ile Arg Glu Lys
225                 230                 235                 240

Gly Lys Val Thr Trp Gly Leu Val Tyr Ala Thr Arg Arg Leu Ser Leu
                245                 250                 255

Gly Arg Val Pro Val Arg Leu Ser Val Arg Asp Gly Arg Gln Ala Gln
            260                 265                 270

Glu Glu His Ser Glu His Arg Leu Val Glu Val Gly Gln Gly Ser Leu
        275                 280                 285

Gln His Lys Glu Gly Thr Arg Gln Arg Arg Pro Ala Arg Gly Gly Asp
    290                 295                 300

Lys Gln Leu Arg Thr Leu Arg Glu Gly Ser Pro Pro Arg Gln Arg Pro
305                 310                 315                 320

Arg Ser Glu Arg Leu Gln Asp Trp Asn Arg Val Glu Gln Asp Leu Ser
                325                 330                 335

Leu Ala Asn Val Val Cys Gly Gly Arg Ala Gly Gln Leu Arg Thr Arg
            340                 345                 350

Glu Gly Arg Gln Asn Arg Arg His Ala Arg Arg Ala Arg Arg Asp Ser
        355                 360                 365

Glu Ser Ser Gly Asp Ser Leu Leu Pro Pro Arg Tyr Arg Ala Pro Gln
    370                 375                 380

Gly Ala Gly Leu Gln Gly His Arg Glu Pro Gln Pro Leu His Ala Pro
385                 390                 395                 400

Pro Leu Ala Ser Arg Ser Asp Asn Arg Glu Gly Glu Gly Pro His Gln
                405                 410                 415

Arg Asp Trp Leu Gly Arg Ala Gly Glu Arg Gly Gly Val Arg Gln Val
            420                 425                 430

Arg Gly Val His Arg Glu Arg Thr Arg Gly Pro Arg Tyr Val Glu His
        435                 440                 445

Leu Gln Arg Ala Asp Gly Arg Cys Gly Ala Arg Leu Pro Arg Ala Leu
    450                 455                 460

Leu Arg Leu Ser Ala Gly Gly Tyr Glu Pro Arg Gly Gly Lys Ala Gly
465                 470                 475                 480

Asn Pro Gln His Asp Lys Arg Pro Arg Thr Gly Leu Gln Asp Asp Lys
                485                 490                 495

Glu Val Arg Gln Gly Lys Gly Arg Gly Phe Pro Leu Arg Gly Arg Gly
            500                 505                 510
```

-continued

```
Arg Asp Asn Leu Gln Gln His Arg Arg Cys Leu Ser Ile Arg Leu Gln
        515                 520                 525

Arg Pro Lys Gly Arg Glu Ser Cys Arg Lys Arg Gln Leu Leu Pro Gln
    530                 535                 540

Arg Ala Leu Leu Arg Arg Asn Pro Gln Gly Gln Ala Gln His Arg Val
545                 550                 555                 560

Arg Arg Asp Leu Arg Gln Ser Ser Ala Ser Gln Gly Glu Arg Leu Asp
                565                 570                 575

Arg Arg Leu Leu His Glu Arg Ser Arg Gln Val Phe Gly Ala Gln Val
            580                 585                 590

Pro Glu His Thr Pro Asp Ile Leu Pro Gly Ser Ser Gln Leu Arg Leu
        595                 600                 605

Arg Leu Gln Ala Arg Glu Phe Phe Arg Arg Arg Lys Ala Arg Lys Arg
    610                 615                 620

His Arg Leu Gly Asp Leu Ser Gly Gly Asp Leu Arg Leu Asp Lys Arg
625                 630                 635                 640

Gly Gln Gln Ile Arg Gly Pro Gly Leu Arg His Arg Lys Arg Asn Ser
                645                 650                 655

Arg Phe Asn His Pro Ala Ala Val Leu Pro Arg Glu Pro Cys Ser Glu
            660                 665                 670

Asp Gly Gly Val Arg Gly Gly Leu Arg Arg Gln Gly Leu Pro Leu Leu
        675                 680                 685

Gly Ala Asp Arg Gln Leu Arg Val Gly Pro Arg Phe Gln Asp Glu Val
    690                 695                 700

Arg Pro Leu Ser Gly Ser His Asn Gln Gly Glu Asn Thr Ala Gly Gly
705                 710                 715                 720

Lys Arg Lys Gly Leu Gly His Arg Gly Glu Gln Arg Ser Glu Gln Gly
                725                 730                 735

Asn Pro Gly Glu Val Arg Thr Trp Val Lys Val Met Lys Thr Ile Ala
            740                 745                 750

Val Asp Glu Asp Thr Trp Glu Ala Arg Ser Arg Ser Gly Leu Arg Gln
        755                 760                 765

Ile Val Arg Arg Ser Pro Glu Lys Ala His Thr Gly Leu Asp Arg Val
    770                 775                 780

Asp Ser Thr Arg Pro Arg Ala Ala Thr Thr Arg Arg Pro Ser Ser Cys
785                 790                 795                 800

Ser Thr Ser Arg Thr Arg Arg Arg Glu Asp Arg Val Met Lys Arg Leu
                805                 810                 815

Pro Glu Arg Val Ser Phe Asp Pro Glu Ala Phe Val Glu Ile Asn Arg
            820                 825                 830

Lys Arg Asn Arg Asp Phe Leu Glu Phe Leu Leu Ala Glu Phe Gln Val
        835                 840                 845

Xaa Val Ser Phe Phe Thr Val His Pro Tyr Leu Leu Gly Lys Thr Tyr
    850                 855                 860

Leu Gly Arg Asp Leu Glu Ser Glu Val Arg Ala Leu Asn Glu Ala Tyr
865                 870                 875                 880

Thr Ile Val Tyr Pro Thr Lys Glu Leu Leu Met Arg Ala Ile Glu Ile
                885                 890                 895

Glu Ala Arg Leu Ile Lys Arg Gly Ile Phe Leu Ser Phe Asp Asp Ile
            900                 905                 910

Val Ile Gly Val Thr Ala Ile Glu Asn Asn Ala Leu Leu Val Ser Ser
        915                 920                 925
```

-continued

```
Ala Pro Ser Arg Tyr Arg Pro Leu Glu Lys Tyr Gly Leu Asn Val Met
    930                 935                 940

Gly Leu Lys Leu Leu Leu Arg Arg Thr Pro Glu Ala Arg Pro Glu Gly
945                 950                 955                 960

Ser Arg Gln Met Gly Gly Ala Pro Gly Gly Ile Phe Ser Arg Thr Arg
                965                 970                 975

Met Asn Ala Ile Leu Gly Lys Ser Gln Arg Arg Leu Leu Ala Leu Lys
            980                 985                 990

Pro Leu Ser Ser Asn Ser Pro Leu Ser Ser Ser Gly Glu Gly Lys Ala
        995                 1000                1005

Ser Ile Glu Leu Thr Arg Cys Ser Ala Phe Ser Leu Pro Val Val Ser
    1010                1015                1020

Phe Pro Met Arg Gly Thr Thr Val Leu Val Ser Gln Ala Ile Phe Pro
1025                1030                1035                1040

Arg Ser Glu Gly Phe Phe Glu Asn Ser Arg Ile Thr Ser Leu Pro Pro
                1045                1050                1055

Gly Phe Arg Thr Arg Trp Ser Ser Ser Ile Ala Phe Ser Leu Ser Glu
            1060                1065                1070

Lys Xaa Leu Arg Ser Glu Ala Thr Leu Thr Met Ser Xaa Leu Pro Ser
        1075                1080                1085

Gly Xaa Ile Ser Ser Ala Leu Pro Thr Leu Ser Leu Ala Xaa Gly Thr
    1090                1095                1100

Phe Leu Pro Ala Ile Leu Ser Ile Ser Ser Leu Gln Ser Arg Pro Asn
1105                1110                1115                1120

Tyr Ala Arg Gln Val Ser Leu Phe Lys Pro Leu Pro His Ala Glu His
                1125                1130                1135

His Val Pro Gly Ser Ala Gly His Val Lys Asp Phe Arg Pro Phe Ala
            1140                1145                1150

Asn Leu Lys Gly Leu Gln Asn Leu Leu Ala Gly Leu Phe Pro Pro Gln
        1155                1160                1165

Pro Val Glu Thr Glu Ala Tyr Gln Pro Val Gly Ile Val Ala Leu Arg
    1170                1175                1180

Asn Ala Val Lys Glu Leu Pro Tyr Gln Ala Pro Pro Ser Arg Gly Pro
1185                1190                1195                1200

Ser Leu Ser Ser Arg Ala Phe Arg Leu Gly Lys Pro Cys Pro Gln Phe
                1205                1210                1215

Arg Ala Pro Arg Ala Gly Ala Arg Arg Pro Glu Arg Leu Phe Gln Asn
            1220                1225                1230

Trp Leu Ile Pro Glu Leu Trp Lys Glu Val Leu Leu Trp Ser Ala Arg
        1235                1240                1245

Arg Gly Arg Arg Ala Arg Pro Glu Ser Gly His Arg Ser Pro Ala Gly
    1250                1255                1260

Arg Ala Gly Glu Lys Phe Phe Ser Ser Ser Pro Arg Ser Leu Pro Leu
1265                1270                1275                1280

Asp Arg Gly Arg Gly Ser Ser Pro Gly Arg Val Ser Pro Arg Ile Arg
                1285                1290                1295

Ala Cys Thr Pro Phe Pro Ser Gly Pro Ala Gly Arg Arg Cys Pro Ala
            1300                1305                1310

Ser Ser Thr Ala Glu Gly Ser Pro Pro Asp Arg Gly Arg Arg Gly Ser
        1315                1320                1325

Ser Gln Arg Pro Arg Pro Ser Pro Gly Ser Gln Leu Arg Pro Lys Ser
    1330                1335                1340

Ser Arg Gly Cys Ser Phe Pro Ser Arg Ser Ala Arg Gly Arg Pro Pro
```

-continued

```
1345                1350                1355                1360

 Arg Arg Pro Pro Gln Gly Pro Arg Arg Val Trp Ala His Arg Thr Phe
                1365                1370                1375

 Gly Ser Ser Pro Val Pro Ala Phe His Pro Phe Leu Asp Leu Leu Arg
            1380                1385                1390

 Ser Ser Trp Ser Arg Val Ile Met Ser Arg Ile Lys Ser Ser Ala Gln
        1395                1400                1405

 Ala Lys Thr Pro Ala Leu Ile Pro Lys Ser Glu Thr Ser Trp Pro Ile
    1410                1415                1420

 Pro Pro Ala Glu Pro Lys Ala Ser Ala Thr Thr Leu Ile Leu Ser Ala
1425                1430                1435                1440

 Ile Pro Arg Ala Thr Leu Pro Ala Glu Thr Ile Ser Gly Ser Val Pro
                1445                1450                1455

 Gly Thr Met Lys Cys Arg Ser Ser Phe Glu Gly Leu Arg Arg Thr Ile
            1460                1465                1470

 Ser Gly Arg Tyr Phe Ser Ile Thr Phe Ser Leu Glu Leu Thr Pro
        1475                1480                1485
```

(2) INFORMATION FOR SEQ ID NO: 3:

(i) SEQUENCE CHARACTERISTICS:
(A) LENGTH: 4463 base pairs
(B) TYPE: nucleic acid
(C) STRANDEDNESS: single
(D) TOPOLOGY: linear (ii) MOLECULE TYPE: Genomic DNA (ix) FEATURE:
(A) NAME/KEY: Coding Sequence
(B) LOCATION: 1...4461

(xi) SEQUENCE DESCRIPTION: SEQ ID NO: 3:

```
 AAT TCC AGG ATG AAC CTC ATC TGG TCG GTC TTG AGC TTG TAC ATT CCG      48
 Asn Ser Arg Met Asn Leu Ile Trp Ser Val Leu Ser Leu Tyr Ile Pro
   1               5                  10                  15

 GAA CCG ATG GGG TTC TCG CTG TTG GCG TAC TTT ATC GGG TCT TTG ATG      96
 Glu Pro Met Gly Phe Ser Leu Leu Ala Tyr Phe Ile Gly Ser Leu Met
              20                  25                  30

 TCC TTC CAG ATG TGC TCA GGG ACG ATC GGG ATC TGG AGC CAG TCC CAC     144
 Ser Phe Gln Met Cys Ser Gly Thr Ile Gly Ile Trp Ser Gln Ser His
          35                  40                  45

 TCC GCG TGC GGA TCG CTG AAG ATG AAA TCA ACG GTT CTG TCG TCA ACG     192
 Ser Ala Cys Gly Ser Leu Lys Met Lys Ser Thr Val Leu Ser Ser Thr
      50                  55                  60

 ACC TTG ACC TCC TTG AGC CAG CCC CAA ACG CTC GAG AAG GAG GCA CCG     240
 Thr Leu Thr Ser Leu Ser Gln Pro Gln Thr Leu Glu Lys Glu Ala Pro
  65                  70                  75                  80

 GTG TGG TTC TTC GCG AGG AAG GTG AAC TTA ACG TCT TCA GCG GTT AGG     288
 Val Trp Phe Phe Ala Arg Lys Val Asn Leu Thr Ser Ser Ala Val Arg
                  85                  90                  95

 GGC TTT CCG TCC TGC CAG GTT AGG CCC TCC TTC AGC TTG ACC TCG GTG     336
 Gly Phe Pro Ser Cys Gln Val Arg Pro Ser Phe Ser Leu Thr Ser Val
             100                 105                 110

 TTG TCG TTG ATC CAC TTC CCA GAC TCG GCC AGC CAG GGA ATG AGC TGG     384
 Leu Ser Leu Ile His Phe Pro Asp Ser Ala Ser Gln Gly Met Ser Trp
         115                 120                 125

 TCC TTC AGC GGG TCG AAG AAC AGG GGC TCG ATG AGG CTA TCG TGC CTG     432
 Ser Phe Ser Gly Ser Lys Asn Arg Gly Ser Met Arg Leu Ser Cys Leu
     130                 135                 140
```

-continued

```
CTG CGG CCC AGG AGA CAA GGG GAT AGT TCG TCG GCT GAC TCC ACA GAC      480
Leu Arg Pro Arg Arg Gln Gly Asp Ser Ser Ser Ala Asp Ser Thr Asp
145                 150                 155                 160

CGC CTC CAA CGT AGA GGG TTT CAT TCC TGG GAA GCT CCT CGG CGC GGA      528
Arg Leu Gln Arg Arg Gly Phe His Ser Trp Glu Ala Pro Arg Arg Gly
                165                 170                 175

CGT AGC CCG CGA ATC CAA CAA GGC TTG AAA CCA TCA GCA CTG CCA GCA      576
Arg Ser Pro Arg Ile Gln Gln Gly Leu Lys Pro Ser Ala Leu Pro Ala
            180                 185                 190

GCA AAC CAA GGA TTC GTC TCA TGC GCA CCA CCC CAG ACC GCG AGG GTC      624
Ala Asn Gln Gly Phe Val Ser Cys Ala Pro Pro Gln Thr Ala Arg Val
        195                 200                 205

TGT AGT TAT AAA AAC GCG CTC CAA ATT TAT AAA ACT TTG GGT TCT GTT      672
Cys Ser Tyr Lys Asn Ala Leu Gln Ile Tyr Lys Thr Leu Gly Ser Val
    210                 215                 220

ATA AAA TTG GGG CAA AAA TTA AAA TCG GCA AAC CTT ATA AGG GAG AAA      720
Ile Lys Leu Gly Gln Lys Leu Lys Ser Ala Asn Leu Ile Arg Glu Lys
225                 230                 235                 240

GGC AAA GTT ACA TGG GGG TTG GTC TAT GCT ACC AGA AGG CTT TCT CTG      768
Gly Lys Val Thr Trp Gly Leu Val Tyr Ala Thr Arg Arg Leu Ser Leu
                245                 250                 255

GGG CGT GTC CCA GTC CGG CTT TCA GTT CGA GAT GGG CGA CAA GCT CAG      816
Gly Arg Val Pro Val Arg Leu Ser Val Arg Asp Gly Arg Gln Ala Gln
            260                 265                 270

GAG GAA CAT TCC GAA CAC AGA CTG GTG GAA GTG GGT CAG GGA TCC CTT      864
Glu Glu His Ser Glu His Arg Leu Val Glu Val Gly Gln Gly Ser Leu
        275                 280                 285

CAA CAT AAA GAG GGA ACT CGT CAG CGG CGA CCT GCC CGA GGA GGG GAT      912
Gln His Lys Glu Gly Thr Arg Gln Arg Arg Pro Ala Arg Gly Gly Asp
    290                 295                 300

AAA CAA CTA CGA ACT TTA CGA GAA GGA TCA CCG CCT CGC CAG AGA CCT      960
Lys Gln Leu Arg Thr Leu Arg Glu Gly Ser Pro Pro Arg Gln Arg Pro
305                 310                 315                 320

CGG TCT GAA CGT TTA CAG GAT TGG AAT AGA GTG GAG CAG GAT CTT TCC     1008
Arg Ser Glu Arg Leu Gln Asp Trp Asn Arg Val Glu Gln Asp Leu Ser
                325                 330                 335

CTG GCC AAC GTG GTT TGT GGA GGT CGT GCG GGA CAG CTA CGG ACT CGT     1056
Leu Ala Asn Val Val Cys Gly Gly Arg Ala Gly Gln Leu Arg Thr Arg
            340                 345                 350

GAA GGA CGT CAA AAT CGA AGA CAC GCT CGA AGA GCT CGA CGA GAT AGC     1104
Glu Gly Arg Gln Asn Arg Arg His Ala Arg Arg Ala Arg Arg Asp Ser
        355                 360                 365

GAA TCA TCA GGA GAT AGC CTA CTA CCG CCG CGT TAT AGA GCA CCT CAG     1152
Glu Ser Ser Gly Asp Ser Leu Leu Pro Pro Arg Tyr Arg Ala Pro Gln
    370                 375                 380

GGA GCT GGG CTT CAA GGT CAT CGT GAA CCT CAA CCA CTT CAC GCT CCC     1200
Gly Ala Gly Leu Gln Gly His Arg Glu Pro Gln Pro Leu His Ala Pro
385                 390                 395                 400

CCT CTG GCT TCA CGA TCC GAT AAT CGC GAG GGA GAA GGC CCT CAC CAA     1248
Pro Leu Ala Ser Arg Ser Asp Asn Arg Glu Gly Glu Gly Pro His Gln
                405                 410                 415

CGG GAT TGG CTG GGT CGG GCA GGA GAG CGT GGT GGA GTT CGC CAA GTA     1296
Arg Asp Trp Leu Gly Arg Ala Gly Glu Arg Gly Gly Val Arg Gln Val
            420                 425                 430

CGC GGC GTA CAT CGC GAA CGC ACT CGG GGA CCT CGT TAT GTG GAG CAC     1344
Arg Gly Val His Arg Glu Arg Thr Arg Gly Pro Arg Tyr Val Glu His
        435                 440                 445

CTT CAA CGA GCC GAT GGT CGT TGT GGA GCT CGG TTA CCT CGC GCC CTA     1392
Leu Gln Arg Ala Asp Gly Arg Cys Gly Ala Arg Leu Pro Arg Ala Leu
    450                 455                 460
```

-continued

```
CTC CGG CTT TCC GCC GGG GGT TAT GAA CCC CGA GGC GGC AAA GCT GGC    1440
Leu Arg Leu Ser Ala Gly Gly Tyr Glu Pro Arg Gly Gly Lys Ala Gly
465                 470                 475                 480

AAT CCT CAA CAT GAT AAA CGC CCA CGC ACT GGC CTA CAA GAT GAT AAA    1488
Asn Pro Gln His Asp Lys Arg Pro Arg Thr Gly Leu Gln Asp Asp Lys
                485                 490                 495

GAA GTT CGA CAG GGT AAA GGC CGA GGA TTC CCG CTC CGA GGC CGA GGT    1536
Glu Val Arg Gln Gly Lys Gly Arg Gly Phe Pro Leu Arg Gly Arg Gly
            500                 505                 510

CGG GAT AAT CTA CAA CAA CAT AGG CGT TGC CTA TCC ATA CGA CTC CAA    1584
Arg Asp Asn Leu Gln Gln His Arg Arg Cys Leu Ser Ile Arg Leu Gln
        515                 520                 525

CGA CCC AAA GGA CGT GAA AGC TGC AGA AAA CGA CAA CTA CTT CCA CAG    1632
Arg Pro Lys Gly Arg Glu Ser Cys Arg Lys Arg Gln Leu Leu Pro Gln
    530                 535                 540

CGG GCT CTT CTT CGA CGC AAT CCA CAA GGG CAA GCT CAA CAT CGA GTT    1680
Arg Ala Leu Leu Arg Arg Asn Pro Gln Gly Gln Ala Gln His Arg Val
545                 550                 555                 560

CGA CGG GAC CTT CGT CAA AGT TCG GCA TCT CAG GGG GAA CGA CTG GAG    1728
Arg Arg Asp Leu Arg Gln Ser Ser Ala Ser Gln Gly Glu Arg Leu Asp
                565                 570                 575

AGG CGT CTA CTA CAC GAG AGA AGT CGT CAG GTA TTC GGA GCC CAA GTT    1776
Arg Arg Leu Leu His Glu Arg Ser Arg Gln Val Phe Gly Ala Gln Val
            580                 585                 590

CCC GAG CAT ACC CCT GAT ATC CTT CCG GGG AGT TCA CAA CTA CGG CTA    1824
Pro Glu His Thr Pro Asp Ile Leu Pro Gly Ser Ser Gln Leu Arg Leu
        595                 600                 605

CGC CTG CAG GCC CGG GAG TTC TTC CGC CGA CGG AAG GCC CGT AAG CGA    1872
Arg Leu Gln Ala Arg Glu Phe Phe Arg Arg Arg Lys Ala Arg Lys Arg
    610                 615                 620

CAT CGG CTG GGA GAT CTA TCC GGA GGG GAT CTA CGA CTC GAT AAG AGA    1920
His Arg Leu Gly Asp Leu Ser Gly Gly Asp Leu Arg Leu Asp Lys Arg
625                 630                 635                 640

GGC CAA CAA ATA CGG GGT CCC GGT TTA CGT CAC CGA AAA CGG AAT AGC    1968
Gly Gln Gln Ile Arg Gly Pro Gly Leu Arg His Arg Lys Arg Asn Ser
                645                 650                 655

CGA TTC AAC CAC CCT GCG GCC GTA CTA CCT CGC GAG CCA TGT AGC GAA    2016
Arg Phe Asn His Pro Ala Ala Val Leu Pro Arg Glu Pro Cys Ser Glu
            660                 665                 670

GAT GGA GGC GTA CGA GGC GGG TTA CGA CGT CAG GGG CTA CCT CTA CTG    2064
Asp Gly Gly Val Arg Gly Gly Leu Arg Arg Gln Gly Leu Pro Leu Leu
        675                 680                 685

GGC GCT GAC CGA CAA CTA CGA GTG GGC CCT CGG TTT CAG GAT GAG GTT    2112
Gly Ala Asp Arg Gln Leu Arg Val Gly Pro Arg Phe Gln Asp Glu Val
    690                 695                 700

CGG CCT CTA AGT GGA TCT CAT AAC CAA GGA GAG AAC ACC GCG GGA GGA    2160
Arg Pro Leu Ser Gly Ser His Asn Gln Gly Glu Asn Thr Ala Gly Gly
705                 710                 715                 720

AAG CGT AAA GGT TTA GGG CAT CGT GGA GAA CAA CGG AGT GAG CAA GGA    2208
Lys Arg Lys Gly Leu Gly His Arg Gly Glu Gln Arg Ser Glu Gln Gly
                725                 730                 735

AAT CCG GGA GAA GTT CGG ACT TGG GTG AAG GTA ATG AAG ACG ATA GCC    2256
Asn Pro Gly Glu Val Arg Thr Trp Val Lys Val Met Lys Thr Ile Ala
            740                 745                 750

GTC GAT GAG GAC ACT TGG GAG GCA AGA AGC AGG TCA GGC TTG AGG CAG    2304
Val Asp Glu Asp Thr Trp Glu Ala Arg Ser Arg Ser Gly Leu Arg Gln
        755                 760                 765

ATC GTA CGA CGA AGT CCT GAA AAA GCT CAT ACA GGC CTG GAC AGG GTT    2352
Ile Val Arg Arg Ser Pro Glu Lys Ala His Thr Gly Leu Asp Arg Val
```

-continued

```
    770                 775                 780

GAC TCG ACA AGG CCG AGA GCG GCA ACG ACG AGG AGG CCG AGC TCA TGC    2400
Asp Ser Thr Arg Pro Arg Ala Ala Thr Thr Arg Arg Pro Ser Ser Cys
785                 790                 795                 800

TCA ACC TCA AGA ACA AGA AGA CGG GAG GAC AGG GTA ATG AAG AGA CTC    2448
Ser Thr Ser Arg Thr Arg Arg Arg Glu Asp Arg Val Met Lys Arg Leu
                805                 810                 815

CCT GAG AGG GTC TCT TTC GAT CCC GAG GCG TTC GTT GAG ATA AAC CGA    2496
Pro Glu Arg Val Ser Phe Asp Pro Glu Ala Phe Val Glu Ile Asn Arg
            820                 825                 830

AAG AGA AAC AGG GAC TTT TTA GAG TTC CTC TTG GCG GAG TTC CAG GTG    2544
Lys Arg Asn Arg Asp Phe Leu Glu Phe Leu Leu Ala Glu Phe Gln Val
        835                 840                 845

NCG GTT TCC TTC TTC ACG GTT CAT CCA TAC CTC CTC GGC AAG ACC TAT    2592
Xaa Val Ser Phe Phe Thr Val His Pro Tyr Leu Leu Gly Lys Thr Tyr
    850                 855                 860

CTG GGC AGG GAC CTG GAA AGC GAA GTT CGG GCC CTC AAC GAA GCC TAC    2640
Leu Gly Arg Asp Leu Glu Ser Glu Val Arg Ala Leu Asn Glu Ala Tyr
865                 870                 875                 880

ACC ATC GTG TAT CCC ACG AAA GAA CTC CTC ATG AGG GCC ATA GAA ATC    2688
Thr Ile Val Tyr Pro Thr Lys Glu Leu Leu Met Arg Ala Ile Glu Ile
                885                 890                 895

GAG GCG AGG CTG ATA AAA AGG GGA ATT TTT CTC TCT TTC GAC GAC ATC    2736
Glu Ala Arg Leu Ile Lys Arg Gly Ile Phe Leu Ser Phe Asp Asp Ile
            900                 905                 910

GTC ATT GGA GTA ACT GCC ATT GAA AAC AAC GCC CTT CTC GTG AGC TCT    2784
Val Ile Gly Val Thr Ala Ile Glu Asn Asn Ala Leu Leu Val Ser Ser
        915                 920                 925

GCC CCC TCA CGC TAC AGG CCC CTT GAG AAG TAC GGG CTC AAC GTT ATG    2832
Ala Pro Ser Arg Tyr Arg Pro Leu Glu Lys Tyr Gly Leu Asn Val Met
    930                 935                 940

GGG CTC AAG CTC CTT CTT CGA CGA ACT CCG GAA GCT CGC CCG GAA GGA    2880
Gly Leu Lys Leu Leu Leu Arg Arg Thr Pro Glu Ala Arg Pro Glu Gly
945                 950                 955                 960

AGC CGC CAG ATG GGA GGT GCC CCC GGT GGG ATC TTC TCC AGA ACG AGA    2928
Ser Arg Gln Met Gly Gly Ala Pro Gly Gly Ile Phe Ser Arg Thr Arg
                965                 970                 975

ATG AAC GCT ATC CTC GGG AAG AGC CAG CGG AGG CTT CTC GCC CTA AAG    2976
Met Asn Ala Ile Leu Gly Lys Ser Gln Arg Arg Leu Leu Ala Leu Lys
            980                 985                 990

CCC CTC TCC TCG AAC TCC CCC CTA AGC TCC TCC GGT GAG GGA AAG GCG    3024
Pro Leu Ser Ser Asn Ser Pro Leu Ser Ser Ser Gly Glu Gly Lys Ala
        995                1000                1005

TCT ATC GAG CTG ACA AGG TGT TCG GCT TTC TCG TTG CCC GTC GTC AGC    3072
Ser Ile Glu Leu Thr Arg Cys Ser Ala Phe Ser Leu Pro Val Val Ser
   1010                1015                1020

TTT CCG ATG AGG GGA ACA ACC GTT CTC GTG AGC CAG GCC ATC TTT CCA    3120
Phe Pro Met Arg Gly Thr Thr Val Leu Val Ser Gln Ala Ile Phe Pro
1025                1030                1035                1040

AGG AGC GAG GGG TTC TTT GAG AAC TCG AGG ATT ACG AGC CTT CCT CCC    3168
Arg Ser Glu Gly Phe Phe Glu Asn Ser Arg Ile Thr Ser Leu Pro Pro
               1045                1050                1055

GGC TTC AGA ACA CGG TGG AGC TCC TCT ATA GCT TTT TCC CTA TCG GAG    3216
Gly Phe Arg Thr Arg Trp Ser Ser Ser Ile Ala Phe Ser Leu Ser Glu
           1060                1065                1070

AAG NTT CTG AGG TCG GAG GCG ACG CTG ACA ATG TCG NAG CTC CCG TCC    3264
Lys Xaa Leu Arg Ser Glu Ala Thr Leu Thr Met Ser Xaa Leu Pro Ser
       1075                1080                1085

GGA GNC ATT TCT TCC GCC CTG CCA ACG CTC AGC CTC GCG NAG GGG ACC    3312
```

-continued

```
Gly Xaa Ile Ser Ser Ala Leu Pro Thr Leu Ser Leu Ala Xaa Gly Thr
   1090                1095                1100

TTT CTC CCC GCT ATC CTG AGC ATC TCC TCG CTG CAG TCG AGG CCG AAC      3360
Phe Leu Pro Ala Ile Leu Ser Ile Ser Ser Leu Gln Ser Arg Pro Asn
1105                1110                1115                1120

TAC GCC CGA CAG GTT TCT CTT TTC AAG CCT CTT CCT CAT GCA GAG CAT      3408
Tyr Ala Arg Gln Val Ser Leu Phe Lys Pro Leu Pro His Ala Glu His
                1125                1130                1135

CAT GTC CCT GGT TCC GCA GGC CAC GTC AAG GAT TTT CGG CCT TTC GCG      3456
His Val Pro Gly Ser Ala Gly His Val Lys Asp Phe Arg Pro Phe Ala
            1140                1145                1150

AAC CTC AAG GGA CTT CAA AAC CTC CTC GCA GGC CTT TTT CCT CCA CAA      3504
Asn Leu Lys Gly Leu Gln Asn Leu Leu Ala Gly Leu Phe Pro Pro Gln
        1155                1160                1165

CCT GTC GAG ACT GAG GCT TAT CAG CCT GTT GGT ATC GTA GCG CTC CGC      3552
Pro Val Glu Thr Glu Ala Tyr Gln Pro Val Gly Ile Val Ala Leu Arg
    1170                1175                1180

AAT GCT GTC AAA GAG CTC CCT TAC CAA GCT CCT CCC TCC CGA GGA CCT      3600
Asn Ala Val Lys Glu Leu Pro Tyr Gln Ala Pro Pro Ser Arg Gly Pro
1185                1190                1195                1200

TCT TTA TCT TCG CGG GCC TTC CGC CTA GGT AAA CCC TGT CCG CAA TTT      3648
Ser Leu Ser Ser Arg Ala Phe Arg Leu Gly Lys Pro Cys Pro Gln Phe
                1205                1210                1215

AGA GCT CCT CGA GCT GGT GCG AGA CGA CCA GAA CGC CTT TTC CAG AAT      3696
Arg Ala Pro Arg Ala Gly Ala Arg Arg Pro Glu Arg Leu Phe Gln Asn
            1220                1225                1230

TGG CTA ATT CCC GAA TTA TGG AAA GAA GTT CTT CTT TGG AGC GCG CGT      3744
Trp Leu Ile Pro Glu Leu Trp Lys Glu Val Leu Leu Trp Ser Ala Arg
        1235                1240                1245

CGA GGC CGG AGG GCT CGT CCA GAA TCA GGA CAT CGA AGT CCA GCA GGG      3792
Arg Gly Arg Arg Ala Arg Pro Glu Ser Gly His Arg Ser Pro Ala Gly
    1250                1255                1260

CGC GCA GGA GAG AAG TTT TTC TCC TCG TCC CCC CGC TCA CTT CCT TTG      3840
Arg Ala Gly Glu Lys Phe Phe Ser Ser Ser Pro Arg Ser Leu Pro Leu
1265                1270                1275                1280

GAT AGA GGT CGA GGT AGT TCT CCA GGC CGA GTC TCT CCA CGT ATT CGA      3888
Asp Arg Gly Arg Gly Ser Ser Pro Gly Arg Val Ser Pro Arg Ile Arg
                1285                1290                1295

GCC TGC ACT CCC TTC CCC AGC GGG CCG GCA GGC AGA CGT TGT CCC GCC      3936
Ala Cys Thr Pro Phe Pro Ser Gly Pro Ala Gly Arg Arg Cys Pro Ala
            1300                1305                1310

TCT TCC ACG GCA GAA GGT AGT CCT CCT GAT AGA GGA CGG AGG GGT TCT      3984
Ser Ser Thr Ala Glu Gly Ser Pro Pro Asp Arg Gly Arg Arg Gly Ser
        1315                1320                1325

TCA CAA AGA CCT CGC CCG AGT CCG GGT TCT CAA CTC CGG CCA AAA TCT      4032
Ser Gln Arg Pro Arg Pro Ser Pro Gly Ser Gln Leu Arg Pro Lys Ser
    1330                1335                1340

TCA CGA GGG TGC TCT TTC CCG TCC CGT TCG GCC CGA GGC CGA CCA CCT      4080
Ser Arg Gly Cys Ser Phe Pro Ser Arg Ser Ala Arg Gly Arg Pro Pro
1345                1350                1355                1360

CGC CGG CCC CCT CAA GGC CCC CGT CGA GTA TGG GCT CAC AGG ACT TTC      4128
Arg Arg Pro Pro Gln Gly Pro Arg Arg Val Trp Ala His Arg Thr Phe
                1365                1370                1375

GGT TCT TCA CCA GTA CCA GCC TTT CAC CCA TTC CTC GAC CTC CTC AGA      4176
Gly Ser Ser Pro Val Pro Ala Phe His Pro Phe Leu Asp Leu Leu Arg
            1380                1385                1390

AGT AGC TGG TCG AGG GTT ATC ATG AGC AGG ATT AAG AGC AGT GCC CAG      4224
Ser Ser Trp Ser Arg Val Ile Met Ser Arg Ile Lys Ser Ser Ala Gln
        1395                1400                1405
```

-continued

GCA AAA ACA CCG GCT TTA ATT CCC AAA TCG GAG ACG AGC TGG CCG ATT 4272
Ala Lys Thr Pro Ala Leu Ile Pro Lys Ser Glu Thr Ser Trp Pro Ile
1410 1415 1420

CCT CCC GCT GAA CCA AAA GCC TCG GCA ACG ACG CTT ATC CTG AGC GCT 4320
Pro Pro Ala Glu Pro Lys Ala Ser Ala Thr Thr Leu Ile Leu Ser Ala
1425 1430 1435 1440

ATT CCC AGG GCG ACT CTG CCT GCC GAG ACC ATC TCG GGG AGC GTT CCC 4368
Ile Pro Arg Ala Thr Leu Pro Ala Glu Thr Ile Ser Gly Ser Val Pro
1445 1450 1455

GGG ACG ATG AAG TGC CGG AGC AGC TTT GAG GGT TTG AGG AGA ACT ATC 4416
Gly Thr Met Lys Cys Arg Ser Ser Phe Glu Gly Leu Arg Arg Thr Ile
1460 1465 1470

AGC GGG CGG TAT TTT TCT ATC ACC TTT TCG CTT GAG CTC ACT CCA GC 4463
Ser Gly Arg Tyr Phe Ser Ile Thr Phe Ser Leu Glu Leu Thr Pro
1475 1480 1485

(2) INFORMATION FOR SEQ ID NO: 4:

(i) SEQUENCE CHARACTERISTICS:
(A) LENGTH: 1487 amino acids
(B) TYPE: amino acid
(D) TOPOLOGY: linear (ii) MOLECULE TYPE: protein (v) FRAGMENT TYPE: internal (xi) SEQUENCE DESCRIPTION: SEQ ID NO: 4:

Asn Ser Arg Met Asn Leu Ile Trp Ser Val Leu Ser Leu Tyr Ile Pro
1 5 10 15

Glu Pro Met Gly Phe Ser Leu Leu Ala Tyr Phe Ile Gly Ser Leu Met
20 25 30

Ser Phe Gln Met Cys Ser Gly Thr Ile Gly Ile Trp Ser Gln Ser His
35 40 45

Ser Ala Cys Gly Ser Leu Lys Met Lys Ser Thr Val Leu Ser Ser Thr
50 55 60

Thr Leu Thr Ser Leu Ser Gln Pro Gln Thr Leu Glu Lys Glu Ala Pro
65 70 75 80

Val Trp Phe Phe Ala Arg Lys Val Asn Leu Thr Ser Ser Ala Val Arg
85 90 95

Gly Phe Pro Ser Cys Gln Val Arg Pro Ser Phe Ser Leu Thr Ser Val
100 105 110

Leu Ser Leu Ile His Phe Pro Asp Ser Ala Ser Gln Gly Met Ser Trp
115 120 125

Ser Phe Ser Gly Ser Lys Asn Arg Gly Ser Met Arg Leu Ser Cys Leu
130 135 140

Leu Arg Pro Arg Arg Gln Gly Asp Ser Ser Ser Ala Asp Ser Thr Asp
145 150 155 160

Arg Leu Gln Arg Arg Gly Phe His Ser Trp Glu Ala Pro Arg Arg Gly
165 170 175

Arg Ser Pro Arg Ile Gln Gln Gly Leu Lys Pro Ser Ala Leu Pro Ala
180 185 190

Ala Asn Gln Gly Phe Val Ser Cys Ala Pro Pro Gln Thr Ala Arg Val
195 200 205

Cys Ser Tyr Lys Asn Ala Leu Gln Ile Tyr Lys Thr Leu Gly Ser Val
210 215 220

Ile Lys Leu Gly Gln Lys Leu Lys Ser Ala Asn Leu Ile Arg Glu Lys
225 230 235 240

-continued

```
Gly Lys Val Thr Trp Gly Leu Val Tyr Ala Thr Arg Arg Leu Ser Leu
                245                 250                 255

Gly Arg Val Pro Val Arg Leu Ser Val Arg Asp Gly Arg Gln Ala Gln
            260                 265                 270

Glu Glu His Ser Glu His Arg Leu Val Glu Val Gly Gln Gly Ser Leu
        275                 280                 285

Gln His Lys Glu Gly Thr Arg Gln Arg Arg Pro Ala Arg Gly Gly Asp
    290                 295                 300

Lys Gln Leu Arg Thr Leu Arg Glu Gly Ser Pro Pro Arg Gln Arg Pro
305                 310                 315                 320

Arg Ser Glu Arg Leu Gln Asp Trp Asn Arg Val Glu Gln Asp Leu Ser
                325                 330                 335

Leu Ala Asn Val Val Cys Gly Gly Arg Ala Gly Gln Leu Arg Thr Arg
            340                 345                 350

Glu Gly Arg Gln Asn Arg Arg His Ala Arg Arg Ala Arg Arg Asp Ser
        355                 360                 365

Glu Ser Ser Gly Asp Ser Leu Leu Pro Pro Arg Tyr Arg Ala Pro Gln
    370                 375                 380

Gly Ala Gly Leu Gln Gly His Arg Glu Pro Gln Pro Leu His Ala Pro
385                 390                 395                 400

Pro Leu Ala Ser Arg Ser Asp Asn Arg Glu Gly Glu Gly Pro His Gln
                405                 410                 415

Arg Asp Trp Leu Gly Arg Ala Gly Glu Arg Gly Gly Val Arg Gln Val
            420                 425                 430

Arg Gly Val His Arg Glu Arg Thr Arg Gly Pro Arg Tyr Val Glu His
        435                 440                 445

Leu Gln Arg Ala Asp Gly Arg Cys Gly Ala Arg Leu Pro Arg Ala Leu
    450                 455                 460

Leu Arg Leu Ser Ala Gly Gly Tyr Glu Pro Arg Gly Gly Lys Ala Gly
465                 470                 475                 480

Asn Pro Gln His Asp Lys Arg Pro Arg Thr Gly Leu Gln Asp Asp Lys
                485                 490                 495

Glu Val Arg Gln Gly Lys Gly Arg Gly Phe Pro Leu Arg Gly Arg Gly
            500                 505                 510

Arg Asp Asn Leu Gln Gln His Arg Arg Cys Leu Ser Ile Arg Leu Gln
        515                 520                 525

Arg Pro Lys Gly Arg Glu Ser Cys Arg Lys Arg Gln Leu Leu Pro Gln
    530                 535                 540

Arg Ala Leu Leu Arg Arg Asn Pro Gln Gly Gln Ala Gln His Arg Val
545                 550                 555                 560

Arg Arg Asp Leu Arg Gln Ser Ser Ala Ser Gln Gly Glu Arg Leu Asp
                565                 570                 575

Arg Arg Leu Leu His Glu Arg Ser Arg Gln Val Phe Gly Ala Gln Val
            580                 585                 590

Pro Glu His Thr Pro Asp Ile Leu Pro Gly Ser Ser Gln Leu Arg Leu
        595                 600                 605

Arg Leu Gln Ala Arg Glu Phe Phe Arg Arg Arg Lys Ala Arg Lys Arg
    610                 615                 620

His Arg Leu Gly Asp Leu Ser Gly Gly Asp Leu Arg Leu Asp Lys Arg
625                 630                 635                 640

Gly Gln Gln Ile Arg Gly Pro Gly Leu Arg His Arg Lys Arg Asn Ser
                645                 650                 655

Arg Phe Asn His Pro Ala Ala Val Leu Pro Arg Glu Pro Cys Ser Glu
```

-continued

```
            660                 665                 670

Asp Gly Gly Val Arg Gly Gly Leu Arg Arg Gln Gly Leu Pro Leu Leu
        675                 680                 685

Gly Ala Asp Arg Gln Leu Arg Val Gly Pro Arg Phe Gln Asp Glu Val
    690                 695                 700

Arg Pro Leu Ser Gly Ser His Asn Gln Gly Glu Asn Thr Ala Gly Gly
705                 710                 715                 720

Lys Arg Lys Gly Leu Gly His Arg Gly Glu Gln Arg Ser Glu Gln Gly
                725                 730                 735

Asn Pro Gly Glu Val Arg Thr Trp Val Lys Val Met Lys Thr Ile Ala
            740                 745                 750

Val Asp Glu Asp Thr Trp Glu Ala Arg Ser Arg Ser Gly Leu Arg Gln
        755                 760                 765

Ile Val Arg Arg Ser Pro Glu Lys Ala His Thr Gly Leu Asp Arg Val
    770                 775                 780

Asp Ser Thr Arg Pro Arg Ala Ala Thr Thr Arg Arg Pro Ser Ser Cys
785                 790                 795                 800

Ser Thr Ser Arg Thr Arg Arg Arg Glu Asp Arg Val Met Lys Arg Leu
                805                 810                 815

Pro Glu Arg Val Ser Phe Asp Pro Glu Ala Phe Val Glu Ile Asn Arg
            820                 825                 830

Lys Arg Asn Arg Asp Phe Leu Glu Phe Leu Leu Ala Glu Phe Gln Val
        835                 840                 845

Xaa Val Ser Phe Phe Thr Val His Pro Tyr Leu Leu Gly Lys Thr Tyr
    850                 855                 860

Leu Gly Arg Asp Leu Glu Ser Glu Val Arg Ala Leu Asn Glu Ala Tyr
865                 870                 875                 880

Thr Ile Val Tyr Pro Thr Lys Glu Leu Leu Met Arg Ala Ile Glu Ile
                885                 890                 895

Glu Ala Arg Leu Ile Lys Arg Gly Ile Phe Leu Ser Phe Asp Asp Ile
            900                 905                 910

Val Ile Gly Val Thr Ala Ile Glu Asn Asn Ala Leu Leu Val Ser Ser
        915                 920                 925

Ala Pro Ser Arg Tyr Arg Pro Leu Glu Lys Tyr Gly Leu Asn Val Met
    930                 935                 940

Gly Leu Lys Leu Leu Leu Arg Arg Thr Pro Glu Ala Arg Pro Glu Gly
945                 950                 955                 960

Ser Arg Gln Met Gly Gly Ala Pro Gly Gly Ile Phe Ser Arg Thr Arg
                965                 970                 975

Met Asn Ala Ile Leu Gly Lys Ser Gln Arg Arg Leu Leu Ala Leu Lys
            980                 985                 990

Pro Leu Ser Ser Asn Ser Pro Leu Ser Ser Ser Gly Glu Gly Lys Ala
        995                1000                1005

Ser Ile Glu Leu Thr Arg Cys Ser Ala Phe Ser Leu Pro Val Val Ser
   1010                1015                1020

Phe Pro Met Arg Gly Thr Thr Val Leu Val Ser Gln Ala Ile Phe Pro
1025               1030                1035                1040

Arg Ser Glu Gly Phe Phe Glu Asn Ser Arg Ile Thr Ser Leu Pro Pro
               1045                1050                1055

Gly Phe Arg Thr Arg Trp Ser Ser Ser Ile Ala Phe Ser Leu Ser Glu
           1060                1065                1070

Lys Xaa Leu Arg Ser Glu Ala Thr Leu Thr Met Ser Xaa Leu Pro Ser
       1075                1080                1085
```

-continued

```
Gly Xaa Ile Ser Ser Ala Leu Pro Thr Leu Ser Leu Ala Xaa Gly Thr
   1090                1095                1100

Phe Leu Pro Ala Ile Leu Ser Ile Ser Ser Leu Gln Ser Arg Pro Asn
1105                1110                1115                1120

Tyr Ala Arg Gln Val Ser Leu Phe Lys Pro Leu Pro His Ala Glu His
               1125                1130                1135

His Val Pro Gly Ser Ala Gly His Val Lys Asp Phe Arg Pro Phe Ala
           1140                1145                1150

Asn Leu Lys Gly Leu Gln Asn Leu Leu Ala Gly Leu Phe Pro Pro Gln
       1155                1160                1165

Pro Val Glu Thr Glu Ala Tyr Gln Pro Val Gly Ile Val Ala Leu Arg
   1170                1175                1180

Asn Ala Val Lys Glu Leu Pro Tyr Gln Ala Pro Pro Ser Arg Gly Pro
1185                1190                1195                1200

Ser Leu Ser Ser Arg Ala Phe Arg Leu Gly Lys Pro Cys Pro Gln Phe
               1205                1210                1215

Arg Ala Pro Arg Ala Gly Ala Arg Arg Pro Glu Arg Leu Phe Gln Asn
           1220                1225                1230

Trp Leu Ile Pro Glu Leu Trp Lys Glu Val Leu Leu Trp Ser Ala Arg
       1235                1240                1245

Arg Gly Arg Arg Ala Arg Pro Glu Ser Gly His Arg Ser Pro Ala Gly
   1250                1255                1260

Arg Ala Gly Glu Lys Phe Phe Ser Ser Ser Pro Arg Ser Leu Pro Leu
1265                1270                1275                1280

Asp Arg Gly Arg Gly Ser Ser Pro Gly Arg Val Ser Pro Arg Ile Arg
               1285                1290                1295

Ala Cys Thr Pro Phe Pro Ser Gly Pro Ala Gly Arg Arg Cys Pro Ala
           1300                1305                1310

Ser Ser Thr Ala Glu Gly Ser Pro Pro Asp Arg Gly Arg Arg Gly Ser
       1315                1320                1325

Ser Gln Arg Pro Arg Pro Ser Pro Gly Ser Gln Leu Arg Pro Lys Ser
   1330                1335                1340

Ser Arg Gly Cys Ser Phe Pro Ser Arg Ser Ala Arg Gly Arg Pro Pro
1345                1350                1355                1360

Arg Arg Pro Pro Gln Gly Pro Arg Arg Val Trp Ala His Arg Thr Phe
               1365                1370                1375

Gly Ser Ser Pro Val Pro Ala Phe His Pro Phe Leu Asp Leu Leu Arg
           1380                1385                1390

Ser Ser Trp Ser Arg Val Ile Met Ser Arg Ile Lys Ser Ser Ala Gln
       1395                1400                1405

Ala Lys Thr Pro Ala Leu Ile Pro Lys Ser Glu Thr Ser Trp Pro Ile
   1410                1415                1420

Pro Pro Ala Glu Pro Lys Ala Ser Ala Thr Thr Leu Ile Leu Ser Ala
1425                1430                1435                1440

Ile Pro Arg Ala Thr Leu Pro Ala Glu Thr Ile Ser Gly Ser Val Pro
               1445                1450                1455

Gly Thr Met Lys Cys Arg Ser Ser Phe Glu Gly Leu Arg Arg Thr Ile
           1460                1465                1470

Ser Gly Arg Tyr Phe Ser Ile Thr Phe Ser Leu Glu Leu Thr Pro
       1475                1480                1485
```

DIRECTED EVOLUTION OF THERMOPHILIC ENZYMES

This application is a continuation of U.S. application Ser. No. 08/760,489, filed Dec. 5, 1996, now U.S. Pat. No. 5,830,696 which claims benefit of provisional application No. 60/008,311, filed Dec. 7, 1995.

The present invention relates to enzymes, particularly to thermostable enzymes. More particularly, the present invention relates to thermostable enzymes which are stable at high temperature and which have improved activity at lower temperatures.

Thermostable enzymes are enzymes that function at greater than 60° C. Thermostable enzymes are utilized in both industry and biomedical research in assays where certain steps of the assay are performed at significantly increased temperatures. Thermostable enzymes may be obtained from thermophilic organisms found in hot springs, volcanic origin, tropical areas etc. Examples of such organisms, for instance, include prokaryotic microorganisms, such as eubacteria and archaebacteria (Bronneomerier, K. and Staudenbauer, W. L., D. R. Woods (ed), the Clostridia and Biotechnology, Butterworth Publishers, Stoneham, M. A. (1993), among other organisms.

Thermostable enzymes exhibit greater storage life capacity and organic solvent resistance, as compared to their mesophilic counterparts.

There are applications in industry and in research for thermostable enzymes which exhibit enzyme activity at a desired minimum temperature. An example of this occurs in molecular diagnostics wherein reporter molecules must survive long term storage at room temperature or higher or they need to function in unusual environments, and the assays which employ them are performed at room temperature where the activity of thermostable enzymes is generally very low.

FIG. 1 illustrates the full length DNA sequence and corresponding deduced amino acid sequence of Thermococcus 9N2 Beta-glycosidase.

Applicant has found that it is possible to provide thermostable enzymes which have improved activity at lower temperatures.

More particularly, Applicant has found that the activity of thermophilic enzymes can be improved at lower temperatures while maintaining the temperature stability of such enzymes.

Still more particularly, Applicant has found there can be obtained a thermostable enzyme with improved activity at lower temperature by subjecting to mutagenesis a thermostable enzyme or polynucleotide encoding such thermostable enzyme followed by a screening of the resulting mutants to identify a mutated enzyme or a mutated polynucleotide encoding a mutated enzyme, which mutated enzyme retains thermostability and which has an enzyme activity at lower temperatures which is at least two (2) times greater than a corresponding non-mutated enzyme.

The thermostable enzymes and mutated thermostable enzymes are stable at temperatures up to 60° C. and preferably are stable at temperatures of up to 70° C. and more preferably at temperatures up to 95° C. and higher.

Increased activity of mutated thermostable enzymes at lower temperatures is meant to encompass activities which are at least two-fold, preferably at least four-fold, and more preferably at least ten-fold greater than that of the corresponding wild-type enzyme.

Increased enzyme activity at lower temperatures means that enzyme activity is increased at a temperature below 50° C., preferably below 40° C. and more preferably below 30° C.. Thus, in comparing enzyme activity at a lower temperature between the mutated and non-mutated enzyme, the enzyme activity of the mutated enzyme at defined lower temperatures is at least 2 times greater than the enzyme activity of the corresponding non-mutated enzyme.

Thus, lower temperatures and lower temperature ranges include temperatures which are at least 5° C. less than the temperature at which thermostable enzymes are stable, which includes temperatures below 55° C., 50° C., 45° C., 40° C., 35° C., 30° C., 25° C. and 20° C., with below 50° C. being preferred, and below 40 being more preferred, and below 30° C. (or approximately room temperature) being most preferred.

In accordance with an aspect of the present invention, the lower temperature or lower temperature range at which a greater enzyme activity is desired is determined and a thermostable enzyme(s), or polynucleotide encoding such enzyme(s), are subjected to mutagenesis and the resulting mutants are screened to determine mutated enzymes (or polynucleotide encoding mutated enzymes) which retain thermostability and which have a minimum desired increase in enzyme activity at the desired temperature or temperature range.

Thermostable enzymes are enzymes which have activity, i.e. are not degraded, at temperatures above 60° C. Thermostable enzymes also have increased storage life, and high resistance to organic solvents.

Thermostable enzymes may be isolated from thermophilic organisms such as those which are found in elevated temperatures such as in hot springs, volcanic areas and tropical areas. Examples of thermophilic organisms are prokaryotic organisms for example, thermophilic bacteria such as eubacteria and archaebacteria.

The DNA from these thermostable organisms can then be isolated by available techniques that are described in the literature. The IsoQuick® nucleic acid extraction kit (MicroProbe Corporation) is suitable for this purpose.

The term “derived” or “isolated” means that material is removed from its original environment (e.g., the natural environment if it is naturally occurring). For example, a naturally-occurring polynucleotide or polypeptide present in a living animal is not isolated, but the same polynucleotide or polypeptide separated from some or all of the coexisting materials in the natural system, is isolated.

The DNA isolated or derived from these microorganisms can preferably be inserted into a vector. Such vectors are preferably those containing expression regulatory sequences, including promoters, enhancers and the like. Such polynucleotides can be part of a vector and/or a composition and still be isolated, in that such vector or composition is not part of its natural environment.

Alternatively, enzymes not known to have thermostable properties can be screened for such properties by inserting the DNA encoding the enzyme in an expression vector and transforming a suitable host as hereinafter described, such that the enzyme may be expressed and screened for positive thermostable activity.

As representative examples of expression vectors which may be used there may be mentioned viral particles, baculovirus, phage, plasmids, phagemids, cosmids, phosmids, bacterial artificial chromosomes, viral DNA (e.g. vaccinia, adenovirus, foul pox virus, pseudorabies and derivatives of SV40), P1-based artificial chromosomes, yeast plasmids, yeast artificial chromosomes, and any other vectors specific for specific hosts of interest (such as bacillus, aspergillus, yeast, etc.) Thus, for example, the DNA may be included in any one of a variety of expression vectors for expressing a polypeptide. Such vectors include chromosomal, nonchromosomal and synthetic DNA sequences. Large numbers of suitable vectors are known to those of skill in the art, and are commercially available. The following vectors are provided by way of example; Bacterial: pQE70, pQE60, pQE-9 (Qiagen), psiX174, pBluescript SK, pBluescript KS, (Stratagene); pTRC99a, pKK223-3, pKK233-3, pDR540, pRIT2T (Pharmacia); Eukaryotic: PWLNEO, pXT1, pSG (Stratagene) pSVK3, pBPV, pMSG, pSVLSV40 (Pharmacia). Any other plasmid or vector may be used as long as they are replicable and viable in the host.

The DNA derived from a microorganism(s) may be inserted into the vector by a variety of procedures. In general, the DNA sequence is inserted into an appropriate restriction endonuclease site(s) by procedures known in the art. Such procedures and others are deemed to be within the scope of those skilled in the art.

The DNA sequence in the expression vector is operatively linked to an appropriate expression control sequence (s) (promoter) to direct mRNA synthesis. Particular named bacterial promoters include lacI, lacZ, T3, T7, gpt, lambda $P_R$, $P_L$ and trp. Eukaryotic promoters include CMV immediate early, HSV thymidine kinase, early and late SV40, LTRs from retrovirus, and mouse metallothionein-I. Selection of the appropriate vector and promoter is well within the level of ordinary skill in the art. The expression vector also contains a ribosome binding site for translation initiation and a transcription terminator. The vector may also include appropriate sequences for amplifying expression. Promoter regions can be selected from any desired gene using CAT (chloramphenicol transferase) vectors or other vectors with selectable markers.

In addition, the expression vectors preferably contain one or more selectable marker genes to provide a phenotypic trait for selection of transformed host cells such as dihydrofolate reductase or neomycin resistance for eukaryotic cell culture, or such as tetracycline or ampicillin resistance in *E. coli.*

Generally, recombinant expression vectors will include origins of replication and selectable markers permitting transformation of the host cell, e.g., the ampicillin resistance gene of *E. coli* and *S. cerevisiae* TRP1 gene, and a promoter derived from a highly-expressed gene to direct transcription of a downstream structural sequence. Such promoters can be derived from operon encoding glycolytic enzymes such as 3-phosphoglycerate kinase (PGK), α-factor, acid phosphatase, or heat shock proteins, among others. The heterologous structural sequence is assembled in appropriate phase with translation initiation and termination sequences, and preferably, a leader sequence capable of directing secretion of translated protein into the peroplasmic space or extracellular medium.

The DNA selected and isolated as hereinabove described is introduced into a suitable host to prepare a library which is screened for the desired enzyme activity. The selected DNA is preferably already in a vector which includes appropriate control sequences whereby selected DNA which encodes for an enzyme may be expressed, for detection of the desired activity. The host cell can be a higher eukaryotic cell, such as a mammalian cell, or a lower eukaryotic cell, such as a yeast cell, or the host cell can be a prokaryotic cell, such as a bacterial cell. Introduction of the construct into the host cell can be effected by transformation, calcium phosphate transfection, DEAE-Dextran mediated transfection, or electroporation (Davis, L., Dibner, M., Battey, I., Basic Methods in Molecular Biology, (1986)).

As representative examples of appropriate hosts, there may be mentioned: bacterial cells, such as *E. coli*, Streptomyces, *Salmonella typhimurium*; fungal cells, such as yeast; insect cells such as Drosophila S2 and Spodoptera Sf9; animal cells such as CHO, COS or Bowes melanoma; adenoviruses; plant cells, etc. The selection of an appropriate host is deemed to be within the scope of those skilled in the art from the teachings herein.

With particular references to various mammalian cell culture systems that can be employed to express recombinant protein, examples of mammalian expression systems include the COS-7 lines of monkey kidney fibroblasts, described by Gluzman, Cell, 23:175 (1981), and other cell lines capable of expressing a compatible vector, for example, the C127, 3T3, CHO, HeLa 293 and BHK cell lines. Mammalian expression vectors will comprise an origin of replication, a suitable promoter and enhancer, and also any necessary ribosome binding sites, polyadenylation site, splice donor and acceptor sites, transcriptional termination sequences, and 5' flanking nontranscribed sequences. DNA sequences derived from the SV4' splice, and polyadenylation sites may be used to provide the required nontranscribed genetic elements.

Host cells are genetically engineered (transduced or transformed or transfected) with the vectors. The engineered host cells can be cultured in conventional nutrient media modified as appropriate for activating promoters, selecting transformants or amplifying genes. The culture conditions, such as temperature, pH and the like, are those previously used with the host cell selected for expression, and will be apparent to the ordinarily skilled artisan.

The isolated DNA encoding a thermostable enzyme is subjected to mutagenesis techniques, with the preferred type of mutagenesis techniques being set forth below.

The term "error-prone PCR" refers to a process for performing PCR under conditions where the copying fidelity of the DNA polymerase is low, such that a high rate of point mutations is obtained along the entire length of the PCR product. Leung, D. W., et al., Technique, 1:11–15 (1989) and Caldwell, R. C. & Joyce G. F., PCR Methods Applic., 2:28–33 (1992).

The term "oligonucleotide directed mutagenesis" refers to a process which allows for the generation of site-specific mutations in any cloned DNA segment of interest. Reidhaar-Olson, J. F. & Sauer, R. T., et al., Science, 241:53–57 (1988).

The term "assembly PCR" refers to a process which involves the assembly of a PCR product from a mixture of small DNA fragments. A large number of different PCR reactions occur in parallel in the same vial, with the products of one reaction priming the products of another reaction.

The term "sexual PCR mutagenesis" refers to forced homologous recombination between DNA molecules of different but highly related DNA sequence in vitro, caused by random fragmentation of the DNA molecule based on sequence homology, followed by fixation of the crossover by primer extension in a PCR reaction. Stemmer, W. P., PNAS, USA, 91:10747–10751 (1994).

The term "in vivo mutagenesis" refers to a process of generating random mutations in any cloned DNA of interest which involves the propagation of the DNA in a strain of *E. coli* that carries mutations in one or more of the DNA repair pathways. These "mutator" strains have a higher random mutation rate than that of a wild-type parent. Propagating the DNA in one of these strains will eventually generate random mutations within the DNA.

The term "cassette mutagenesis" refers to any process for replacing a small region of a double stranded DNA molecule with a synthetic oligonucleotide "cassette" that differs from the native sequence. The oligonucleotide often contains completely and/or partially randomized native sequence.

The term "recursive ensemble mutagenesis" refers to an algorithm for protein engineering (protein mutagenesis) developed to produce diverse populations of phenotypically related mutants whose members differ in amino acid sequence. This method uses a feedback mechanism to control successive rounds of combinatorial cassette mutagenesis. Arkin, A. P. and Youvan, D. C., PNAS, USA, 89:7811–7815 (1992).

The term "exponential ensemble mutagenesis" refers to a process for generating combinatorial libraries with a high percentage of unique and functional mutants, wherein small groups of residues are randomized in parallel to identify, at each altered position, amino acids which lead to functional proteins, Delegrave, S. and Youvan, D. C., Biotechnology Research, 11:1548–1552 (1993); and random and site-directed mutagenesis, Arnold, F. H., Current Opinion in Biotechnology, 4:450–455 (1993). All of the references mentioned above are hereby incorporated by reference in their entirety.

As can be seen from the above mutagenesis techniques, the DNA encoding an enzyme having the desired activity may be subject to mutagenesis alone, i.e. as naked DNA, or the DNA may be subjected to mutagenesis after insertion into an appropriate vector as hereinabove described. These techniques are referred to as in vitro mutagenesis.

Alternatively, in vivo mutagenesis may be performed wherein the DNA is subjected to mutagenesis while it is within a cell or living organism. A preferred example of this technique utilizes the XL1 Red Strain of *E. Coli* (Stratagene, Inc.) which has its DNA repair genes, MutH, MutL and MutS, deleted such that many different mutations occur in a short time. Up to 10,000 mutations may take place within a 30 hour time span such that an entire mutated DNA library may be prepared from mutated DNA by procedures known in the art.

After an appropriate amount of time to allow mutations to take place, the mutated DNA is excised from the host cell in the case of in vivo mutagenesis and inserted in another appropriate vector and used to transform a non-mutator host, for example, XL1 Blue strain of *E. Coli* after which a mutated DNA library is prepared. In the case of in vitro mutagenesis, if the mutated DNA has previously been inserted in an appropriate expression vector, said vector is then used directly to transform an appropriate non-mutator host for the preparation of a mutated DNA library, if the mutagenized DNA is not in an appropriate expression vector.

A library is prepared for screening by transforming a suitable organism. Hosts, particularly those specifically identified herein as preferred, are transformed by artificial introduction of the vectors containing the mutated DNA by inoculation under conditions conducive for such transformation.

The resultant libraries of transformed clones are then screened for clones which display activity for the enzyme of interest in a phenotypic assay for enzyme activity.

For example, having prepared a multiplicity of clones from DNA mutagenized by one of the techniques described above, such clones are screened for the specific enzyme activity of interest.

For example, the clones containing the mutated DNA are now subject to screening procedures to determine their activity within both higher temperatures and within the desired lower temperature range to identify mutants which have the desired increase in activity within the lower temperature range when compared to the corresponding wild-type thermostable enzyme which is non-mutated.

Positively identified clones, i.e. those which contain mutated DNA sequences which express thermostable enzymes which are thermostable and yet have an increased activity at least two times than the corresponding wild-type enzyme at temperatures within the lower temperature range, are isolated and sequenced to identify the DNA sequence. As an example, phosphatase activity at the desired lower temperature ranges may be identified by exposing the clones, and thus the thermostable enzyme and testing its ability to cleave an appropriate substrate.

In Example 1 phosphatase and β-galactosidase activity are measured by comparing the wild-type enzymes to the enzymes subjected to mutagenesis. As can be seen from the results of Example 1, mutagenesis of a wild-type phosphatase and β-galactosidase thermophilic enzyme produce mutated enzymes which were 3 and 2.5 times more active, respectively, at lower temperatures than the corresponding wild-type enzymes within the lower temperature range of room temperature.

In the case of protein engineering, after subjecting a thermophilic enzyme to mutagenesis, the mutagenized enzyme is screened for the desired activity namely, increased activity at lower temperatures while maintaining activity at the higher temperatures. Any of the known techniques for protein mutagenesis may be employed, with particularly preferred mutagenesis techniques being those discussed above.

As a representative list of enzymes which may be mutagenized in accordance with the aspects of the present invention, there may be mentioned, the following enzymes and their functions:

1 Lipase/Esterase
- a. Enantioselective hydrolysis of esters (lipids)/thioesters
  - 1) Resolution of racemic mixtures
  - 2) Synthesis of optically active acids or alcohols from meso-diesters
- b. Selective syntheses
  - 1) Regiospecific hydrolysis of carbohydrate esters
  - 2) Selective hydrolysis of cyclic secondary alcohols
- c. Synthesis of optically active esters, lactones, acids, alcohols
  - 1) Transesterification of activated/nonactivated esters
  - 2) Interesterification
  - 3) Optically active lactones from hydroxyesters
  - 4) Regio- and enantioselective ring opening of anhydrides
- d. Detergents
- e. Fat/Oil conversion
- f. Cheese ripening 2 Protease
- a. Ester/amide synthesis
- b. Peptide synthesis
- c. Resolution of racemic mixtures of amino acid esters
- d. Synthesis of non-natural amino acids
- e. Detergents/protein hydrolysis 3 Glycosidase/Glycosyl transferase
- a. Sugar/polymer synthesis
- b. Cleavage of glycosidic linkages to form mono, di- and oligosaccharides
- c. Synthesis of complex oligosaccharides
- d. Glycoside synthesis using UDP-galactosyl transferase e. Transglycosylation of disaccharides, glycosyl fluorides, aryl galactosides f. Glycosyl transfer in oligosaccharide synthesis g. Diastereoselective cleavage of β-glucosylsulfoxides h. Asymmetric glycosylations i. Food processing j. Paper processing 4 Phosphatase/Kinase a. Synthesis/hydrolysis of phosphate esters 1) Regio-, enantioselective phosphorylation 2) Introduction of phosphate esters 3) Synthesize phospholipid precursors 4) Controlled polynucleotide synthesis b. Activate biological molecule c. Selective phosphate bond formation without protecting groups 5 Mono/Dioxygenase a. Direct oxyfunctionalization of unactivated organic substrates b. Hydroxylation of alkane, aromatics, steroids c. Epoxidation of alkenes d. Enantioselective sulphoxidation e. Regio- and stereoselective Bayer-Villiger oxidations 6 Haloperoxidase a. Oxidative addition of halide ion to nucleophilic sites b. Addition of hypohalous acids to olefinic bonds c. Ring cleavage of cyclopropanes d. Activated aromatic substrates converted to ortho and para derivatives e. 1.3 diketones converted to 2-halo-derivatives f. Heteroatom oxidation of sulfur and nitrogen containing substrates g. Oxidation of enol acetates, alkynes and activated aromatic rings 7 Lignin peroxidase/Diarylpropane peroxidase a. Oxidative cleavage of C—C bonds b. Oxidation of benzylic alcohols to aldehydes c. Hydroxylation of benzylic carbons d. Phenol dimerization e. Hydroxylation of double bonds to form diols f. Cleavage of lignin aldehydes 8 Epoxide hydrolase a. Synthesis of enantiomerically pure bioactive compounds b. Regio- and enantioselective hydrolysis of epoxide c. Aromatic and olefinic epoxidation by monooxygenases to form epoxides d. Resolution of racemic epoxides e. Hydrolysis of steroid epoxides 9 Nitrile hydratase/nitrilase a. Hydrolysis of aliphatic nitrites to carboxamides b. Hydrolysis of aromatic, heterocyclic, unsaturated aliphatic nitrites to corresponding acids c. Hydrolysis of acrylonitrile d. Production of aromatic and carboxamides, carboxylic acids (nicotinamide, picolinamide, isonicotinamide)

e. Regioselective hydrolysis of acrylic dinitrile f. α-amino acids from α-hydroxynitriles 10 Transaminase a. Transfer of amino groups into oxo-acids 11 Amidase/Acylase a. Hydrolysis of amides, amidines, and other C-N bonds b. Non-natural amino acid resolution and synthesis The present invention is further described by the following examples. The examples are provided solely to illustrate the invention by reference to specific embodiments. These exemplification's, while illustrating certain specific aspects of the invention, do not portray the limitations or circumscribe the scope of the disclosed invention.

EXAMPLE 1

Mutagenesis of Positive Enzyme Activity Clones

Mutagenesis was performed on two different enzymes (alkaline phosphatase and β-glycosidase), using the two different strategies described here, to generate new enzymes which exhibit a higher degree of activity at lower temperatures than the wild-type enzymes.

Alkaline Phosphatase

The XL1-Red strain (Stratagene) was transformed with DNA encoding an alkaline phosphatase (in plasmid pBluescript) from the organism OC9a according to the manufacturer's protocol. A 5 ml culture of LB+0.1 mg/ml ampicillin was inoculated with 200 μl of the transformation. The culture was allowed to grow at 37° C. for 30 hours. A miniprep was then performed on the culture, and screening was performed by transforming 2 μl of the resulting DNA into XL-1 Blue cells (Stratagene) according to the manufacturer's protocol.

Standard Alkaline Phosphatase Screening Assay

→Plate on LB/amp plates→Lift colonies with Duralon UV (Stratagene) or HATF (Millipore) membranes→Lyse in chloroform vapors for 30 seconds→Heat kill for 30 minutes at 85° C.→Develop filter at room temperature in BCIP buffer→Watch as filter develops and identify and pick fastest developing colonies ("positives")→Restreak "positives" onto a BCIP plate.

BCIP Buffer:

20 mm CAPS pH 9.0

1 mm $MgCl_2$ 0.01 mm $ZnCl_2$ 0.1 mg/ml BCIP

The mutated OC9a phosphatase took 10 minutes to develop color and the wild type enzyme took 30 minutes to develop color in the screening assay.

Beta-Glycosidase

This protocol was used to mutagenize DNA encoding Thermococcus 9N2 Beta-Glycosidase. This DNA sequence is set forth in FIG. 1.

PCR 2 microliters dNTP's (10 mM Stocks)

10 microliters 10×PCR Buffer 0.5 microliters pBluescript vector containing Beta-glycosidase DNA (100 nanograms)

20 microliters 3' Primer (100 pmol)

20 microliters 5' Primer (100 pmol)

16 microliters MnCl $4H_20$ (1.25 mM Stock)

24.5 microliters $H_20$ 1 microliter Taq Polymerase (5.0 Units)

100 microliters total

Reaction Cycle

95° C. 15 seconds

58° C. 30 seconds

72° C. 90 seconds 25 cycles (10 minute extension at 72° C.–4° C. incubation)

Run 5 microliters on a 1% agarose gel to check the reaction.

Purify on a Qiaquick column (Qiagen).

Resuspend in 50 microliters $H_2O$.

Restriction Digest 25 microliters purified PCR product 10 microliters NEB Buffer #2

3 microliters Kpn I (1OU/microliter)

3 microliters EcoR1 (20U/microliter)

59 microliters $H_2O$

Cut for 2 hours at 37° C.

Purify on a Qiaquick column (Qiagen).

Elute with 35 microliters $H_2O$.

Ligation 10 microliters Digested PCR product 5 microliters pBluescript Vector (cut with EcoRI/KpnI and phosphatased with shrimp alkaline phosphatase)

4 microliters 5×Ligation Buffer 1 microliter T4 DNA Ligase (BRL)

Ligate overnight.

Transform into M15pREP4 cells using electroporation.

Plate 100 or 200 microliters onto LB amp meth kan plates, grow overnight at 37 degrees celsius.

Beta-Glycosidase Assay

Perform glycosidase assay to screen for mutants as follows. The filter assay uses buffer Z (see recipe below) containing 1 mg/ml of the substrate 5-bromo-4-chloro-3-indolyl-β-o-glucopyranoside (XGLU) (Diagnostic Chemicals Limited or Sigma).

Z-Buffer: (referenced in Miller, J. H. (1992) A Short Course in Bacterial Genetics, p. 445.)

per liter:

$Na_2HPO_4$—$7H_2O$ 16.1 g $NaH_2PO_4$—$H_2O$ 5.5 g

KC1 0.75 g $MgSO_4$—$7H_2O$ 0.246 g β-mercaptoethanol 2.7 ml

Adjust pH to 7.0

(1) Perform colony lifts using Millipore HATF membrane filters.

(2) Lyse colonies with chloroform vapor in 150 mm glass petri dishes.

(3) Transfer filters to 100 mm glass petri dishes containing a piece of Whatman 3MM filter paper saturated with Z buffer containing 1 mg/ml XGLU. After transferring filter bearing lysed colonies to the glass petri dish, maintain dish at room temperature.

(4) "Positives" were observed as blue spots on the filter membranes ("positives" are spots which appear early). Use the following filter rescue technique to retrieve plasmid from lysed positive colony. Use pasteur pipette (or glass capillary tube) to core blue spots on the filter membrane. Place the small filter disk in an Epp tube containing 20 μl water. Incubate the Epp tube at 75° C. for 5 minutes followed by vortexing to elute plasmid DNA off filter. Transform this DNA into electrocompetent E. coli cells. Repeat filter-lift assay on transformation plates to identify "positives." Return transformation plates to 37° C. incubator after filter lift to regenerate colonies. Inoculate 3 ml LBamp liquid with repurified positives and incubate at 37° C. overnight. Isolate plasmid DNA from these cultures and sequence plasmid insert.

The β-glycosidase subjected to mutagenesis acted on XGLU 2.5 times more efficiently than wild-type β-glycosidase.

What is claimed is:

1. A process for providing a thermostable enzyme having improved enzyme activities as compared to a corresponding wild-type enzyme at lower temperatures comprising:

(a) subjecting to random mutagenesis at least one polynucleotide encoding an enzyme which is stable at a temperature of at least 60° C.; and (b) screening mutants produced in (a) for a mutated enzyme or for a polynucleotide encoding a mutated enzyme, wherein the mutated enzyme is stable at a temperature of at least 60° C. and has increased enzyme activity at a lower temperature than that of the corresponding wild-type enzyme at its optimal temperature.

2. The method of claim 1, wherein the enzyme is stable at a temperature of at least 70° C.

3. The method of claim 1, wherein the activity of the mutated enzyme is at least two-fold greater than the corresponding activity of the wild type enzyme.

4. The method of claim 1, wherein the activity of the mutated enzyme is at least four-fold greater than the corresponding activity of the wild type enzyme.

5. The method of claim 1, wherein the activity of the mutated enzyme is at least ten-fold greater than the corresponding activity of the wild type enzyme.

6. The method of claim 1, wherein the enzyme activity is increased at a temperature below at least 50° C.

7. The method of claim 1, wherein the enzyme activity is increased at a temperature below at least 40° C.

8. The method of claim 1, wherein the enzyme activity is increased at a temperature below at least 30° C.

9. The method of claim 1, wherein the mutagenesis is by error-prone PCR.

10. The method of claim 1, wherein the mutagenesis is by oligonucleotide-directed mutagenesis.

11. The method of claim 1, wherein the mutagenesis is by sexual PCR mutagenesis.

12. The method of claim 1, wherein the mutagenesis is by in vivo mutagenesis.

13. The method of claim 1, wherein the mutagenesis is by exponential ensemble mutagenesis.

14. The method of claim 13, wherein the mutagenesis by exponential ensemble mutagenesis is performed in vitro.

15. The method of claim 13, wherein the mutagenesis by exponential ensemble mutagenesis is performed in vivo.

* * * * *